US008653230B2

(12) United States Patent
Xie

(10) Patent No.: US 8,653,230 B2
(45) Date of Patent: Feb. 18, 2014

(54) MONOMERS, OLIGOMERIC COMPLEXES, COORDINATION POLYMERS, AND METHODS FOR THEIR PREPARATION AND USE

(75) Inventor: Yongshu Xie, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 130 days.

(21) Appl. No.: 13/030,344

(22) Filed: Feb. 18, 2011

(65) Prior Publication Data

US 2012/0214962 A1    Aug. 23, 2012

(51) Int. Cl.
*C08G 79/00* (2006.01)
*C07D 401/14* (2006.01)
*C07F 3/06* (2006.01)
*C07F 3/08* (2006.01)
*C07F 3/14* (2006.01)

(52) U.S. Cl.
USPC .............. 528/423; 528/395; 546/264; 546/12

(58) Field of Classification Search
USPC .................................................. 546/264, 12
See application file for complete search history.

(56) References Cited

U.S. PATENT DOCUMENTS

2002/0028351 A1    3/2002    Wang et al.

FOREIGN PATENT DOCUMENTS

| JP | 2000086683 A | 9/1998 |
| JP | 2001135480 A | 5/2001 |

OTHER PUBLICATIONS

Zeng et al (Synthesis, Structures, and Photoluminescence of Zinc(II), Cadmium(II), and Mercury(II) Coordination Polymers Constructed from Two Novel Tetrapyridyl Ligands, Crystal Growth & Design, vol. 10, No. 4, 2010 (Published on Web Feb. 19, 2010)).*

Brown, Kyalamboka a., et al., Two- and three-dimensional divalent metal coordination polymers constructed from 2,2-dimethylsuccinate and dipryridylamine ligands, CrystEngComm, Jul. 1, 2008, vol. 10, No. 7, pp. 846-855, The Royal Society of Chemistry.

Kang, Youngjin et al., Blue luminescent rigid molecular rods bearing N-7-Azaindolyl and 2,2'-Dipyridylamino and their Zn(II) and AG(I) Complexes, Inorganic Chemistry, Mar. 25, 2003, vol. 42, No. 8, pp. 2789-2797, American Chemical Society.

Liu, Yun and Chao-Nan Xu, Influence of calcining temperature on photoluminescence and triboluminescence of europium-doped strontium aluminate particles prepared by sol-gel process, The Journal of Physical Chemistry B, May 1, 2003, vol. 107, No. 17, pp. 3991-3995, American Chemical Society.

Martin, David P., et al., Cadmium glutarate coordination polymers containing hydrogen-bonding capable tethering organodiimines: from double interpenetration to supramolecular cavities containing an unprecedented water tape morphology, Crystal Growth & Design, 2008, vol. 8, No. 8, pp. 3091-3097, American Chemical Society.

Zeng, Sek-Weng Ng and Wei-Hong Zhu, A triple chain coordination polymer constructed from ZnTPP and a bis(4,4'-dipyridylamine ligand, Inorganic Chemistry Communications, 2010, vol. 13, pp. 929-931, Elsevier B.V.

(Continued)

*Primary Examiner* — Randy Gulakowski
*Assistant Examiner* — Rachel Kahn
(74) *Attorney, Agent, or Firm* — Pepper Hamilton LLP

(57) ABSTRACT

Implementations and techniques for preparing and using monomers, oligomeric complexes, and coordination polymers are generally disclosed.

14 Claims, 13 Drawing Sheets

(56) References Cited

OTHER PUBLICATIONS

Wei, Kai-Ju et al., Syntheses, crystal structures and photoluminescent properties of a series of M(II) coordination polymers containing M-X2-M bridges: from 1-D chains to 2-D networks, Crystal Growth & Design, 2006, vol. 6, No. 6, pp. 1341-1350, American Chemical Society.

Shyu, Eric et al., Structural diversity in luminescent three-dimensional cadmium aliphatic dicarboxylate coordination polymers incorporating 4,4'-dipyridylamine: interpenetrated, non-interpenetrated, and self-penetrated networks, Crystal Growth & Design, 2009, vol. 9, No. 5, pp. 2481-2491, American Chemical Society.

Vertical News, Crystal Research, Recent findings in crystal research described by researchers from China University, Journal of Technology, May 4, 2010, pp. 1-2, accessed online via http://www.verticalnews.com/premium_newsletters/Journal-of-Technology/2010-05-04/71144TE.html on Oct. 10, 2011.

Crystal Research, Journal of Technology, May 4, 2010, pp. 2, accessed at http://www.verticalnews.com/premium_newsletters/Journal-of-Technology/2010-05-04/71144TE.html.

Liu, Y., and Xu, C.-N., Influence of Calcining Temperature on Photoluminescence and Triboluminescence of Europium-Doped Strontium Aluminate Particles Prepared by Sol-Gel Process, The Journal of Physical Chemistry B, 2003, vol. 107, Issue 17, pp. 3991-3995.

Wang, Q., et al., A triple chain coordination polymer constructed from ZnTPP and a bis(4,4'-dipyridylamine) ligand, Inorganic Chemistry Communications, Aug. 2010, vol. 13, Issue 8, pp. 929-931.

* cited by examiner

300

```
┌─────────────────────────────────────────────────────────────┐
│ Heat a Mixture of 4,4-dipyridylamine, 1,4-dibromobenze,     │
│ cupric sulfate, anhydrous potassium carbonate, 18-crown-6,  │
│ and diphenyl ether                                          │
│                                                         310 │
└─────────────────────────────────────────────────────────────┘
                              │
                              ▼
┌─────────────────────────────────────────────────────────────┐
│ Cool the Mixture                                            │
│                                                         320 │
└─────────────────────────────────────────────────────────────┘
                              │
                              ▼
┌─────────────────────────────────────────────────────────────┐
│ Dissolve the Solid Into a Solvent                           │
│                                                         330 │
└─────────────────────────────────────────────────────────────┘
                              │
                              ▼
┌─────────────────────────────────────────────────────────────┐
│ Purify the Ligand from the Solvent                          │
│                                                         340 │
└─────────────────────────────────────────────────────────────┘
```

Fig. 3

1300 A computer program product
1302 A signal bearing medium
1304 at least one of one or more instructions for formatting data to instruct a process unit to heat a mixture of 4-4-dipyridylamine, anhydrous potassium carbonate, cupric sulfate, 18-crown-6, anhydrous potassium carbonate and diphenyl ether;

one or more instructions for formatting data to instruct the process unit to heat a mixture of 2,2'-dipyridylamine, (4-bromophenyl)-di(4-pyridyl)amine, anhydrous potassium carbonate, bronze powder, 18-crown-6, and dimethylformamide;

one or more instructions for formatting data to instruct the process unit to cool the mixture to form a solid including the ligand;

one or more instructions for formatting data to instruct the process unit to dissolve the solid into a solvent; or one or more instructions for formatting data to instruct the process unit to purifying a ligand from the solvent.

| 1306 a computer-readable medium | 1308 a recordable medium | 1310 a communications medium |

Fig. 13

MONOMERS, OLIGOMERIC COMPLEXES, COORDINATION POLYMERS, AND METHODS FOR THEIR PREPARATION AND USE

BACKGROUND

Unless otherwise indicated herein, the approaches described in this section are not prior art to the claims in this application and are not admitted to be prior art by inclusion in this section.

Oligomeric complexes and coordination polymers containing metal ions and organic ligands may be used in a wide range of applications including, for example, optoelectronic devices, optical devices, electronic devices, magnetic devices, molecular sensing devices, catalysis and gas adsorption. Also, compounds that exhibit photoluminescence in the solid-state may be used in a wide range of applications including, for example, optoelectronic devices.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings:

FIG. 3 is an illustration of a flow chart of an example method for producing a ligand;

FIG. 13 is an illustration of an example computer program product;

DETAILED DESCRIPTION

Figure 1:
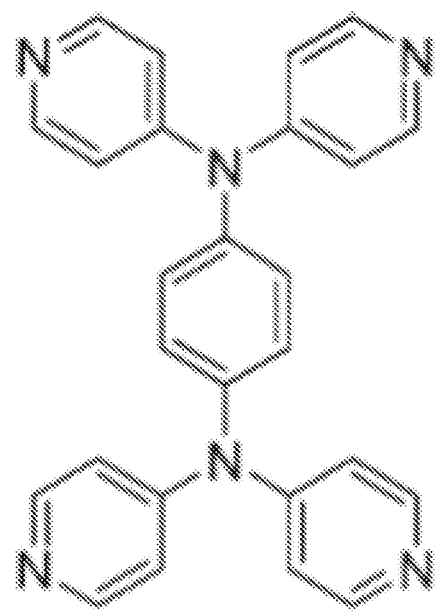
FIG. 1 is an illustration of an example ligand that may be incorporated into a coordination polymer.

The following description sets forth various examples along with specific details to provide a thorough understanding of claimed subject matter. It will be understood by those skilled in the art, however that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Chemical compounds, methods, apparatuses, systems and computer readable media related to oligomeric complexes and coordination polymers are generally disclosed.

It may be desirable to produce oligomeric complexes and coordination polymers that may contain metal ions and organic ligands. Such materials may be used in a wide range of applications including, for example, optoelectronic devices, optical devices, electronic devices, magnetic devices, molecular sensing devices, catalysis, gas adsorption, or the like. Also, it may be desirable to produce solid-state photoluminescent compounds. Such compounds may be used in a wide range of applications including, for example, optoelectronic devices. In some examples, coordination polymers, or oligomeric complexes may include a metal atom or atoms structurally incorporated with a ligand or ligands. In various examples, the metal atom or atoms may be a metal ion or ions. In some examples, the metal atom or atoms may be considered a metal center in the oligomeric complex and the coordination polymer.

Monomer Compounds

In one aspect, various monomer compounds are described. The monomer can generally contain four pyridyl rings. The four pyridyl groups can be defined as pyridyl group $Py^1$, pyridyl group $Py^2$, pyridyl group $Py^3$, and pyridyl group $Py^4$. The compound can generally have a central linker portion covalently attached to the four pyridyl rings. In some examples, the monomer compound can contain a first bipyridylamine group and a second bipyridylamine group. In one example, the central linker portion can be a phenyl group (a benzene ring). In another example, the central linker portion can be a phenylenediamine group. The phenylenediamine structure can have 1,2 (ortho) or 1,3 (meta) or 1,4 (para) orientations of the two amine groups. In some cases, the 1,4 orientation can be selected to reduce steric interactions between the pyridyl rings or to confer a linear configuration to the monomer compound. The 1,4-phenylenediamine can have two pyridyl rings attached at each of the two amine positions. This monomer compound can generally be described as $(Py^1Py^2)N—C_6H_4—N(Py^3Py^4)$. $Py^1$, $Py^2$, $Py^3$, and $Py^4$ can each be the same or different. In some cases, $Py^1$ and $Py^2$ will be the same. In some cases, $Py^3$ and $Py^4$ will be the same. In some cases, $Py^1$, $Py^2$, $Py^3$, and $Py^4$ can all be the same. The pyridyl rings can be attached to the central linker amine at various positions. For example, the pyridyl ring can be attached to the amine at the 2 position (ortho to the pyridinyl nitrogen), at the 3 position (meta to the pyridinyl nitrogen), or at the 4 position (para to the pyridinyl nitrogen). The monomer compound can be symmetric or asymmetric relative to the central linker portion.

In another example, the central linker portion can be a terphenyl group. The terphenyl structure can have 1,2 (ortho) or 1,3 (meta) or 1,4 (para) orientations of the phenyl groups around the central benzene ring. In some cases, the 1,4 orientation can selected. The terphenyl structure can have two pyridyl rings attached at each of the two phenyl groups. The monomer compound can be generally described as $(Py^1Py^2)N—C_6H_4—C_6H_4—C_6H_4—N(Py^3Py^4)$. $Py^1$, $Py^2$, $Py^3$, and $Py^4$ can each be the same or different. In some cases, $Py^1$ and $Py^2$ will be the same. In some cases, $Py^3$ and $Py^4$ will be the same. In some cases, $Py^1$, $Py^2$, $Py^3$, and $Py^4$ can all be the same. The pyridyl rings can be attached to the central linker amine at various positions. The monomer compound can be symmetric or asymmetric relative to the central linker portion.

In another example, the central linker can be a biphenyl group. The biphenyl structure can have two pyridyl rings attached at each of the two phenyl groups. The monomer compound can be generally described as $(Py^1Py^2)N—C_6H_4— —C_6H_4—N(Py^3Py^4)$. $Py^1$, $Py^2$, $Py^3$, and $Py^4$ can each be the same or different. In some cases, $Py^1$ and $Py^2$ will be the same. In some cases, $Py^3$ and $Py^4$ will be the same. In some cases, $Py^1$, $Py^2$, $Py^3$, and $Py^4$ can all be the same. The pyridyl rings can be attached to the central linker amine at various positions. The monomer compound can be symmetric or asymmetric relative to the central linker portion.

In another example, the central linker may be a poly-aromatic hydrocarbon (PAH) group. In general, any suitable PAH may be used as a central linker. The PAH structure can have two pyridyl rings attached at each of the two phenyl groups. The monomer compound can be generally described as $(Py^1Py^2)N-PAH-N(Py^3Py^4)$. $Py^1$, $Py^2$, $Py^3$, and $Py^4$ can each be the same or different. In some cases, $Py^1$ and $Py^2$ will be the same. In some cases, $Py^3$ and $Py^4$ will be the same. In some cases, $Py^1$, $Py^2$, $Py^3$, and $Py^4$ can all be the same. The pyridyl rings can be attached to the central linker at various positions. The monomer compound can be symmetric or asymmetric relative to the central linker portion.

In another example, the central linker may be a (methylbenzene)$_2$ group. The (methylbenzene)$_2$ structure can have two pyridyl rings attached at each of the two phenyl groups. The monomer compound can be generally described as $(Py^1Py^2)N—C_6H_4—CH_2—C_6H_4—N(Py^3Py^4)$. $Py^1$, $Py^2$, $Py^3$, and $Py^4$ can each be the same or different. In some cases, $Py^1$ and $Py^2$ will be the same. In some cases, $Py^3$ and $Py^4$ will be the same. In some cases, $Py^1$, $Py^2$, $Py^3$, and $Py^4$ can all be the same. The pyridyl rings can be attached to the central linker amine at various positions. The monomer compound can be symmetric or asymmetric relative to the central linker portion.

Figure 15:
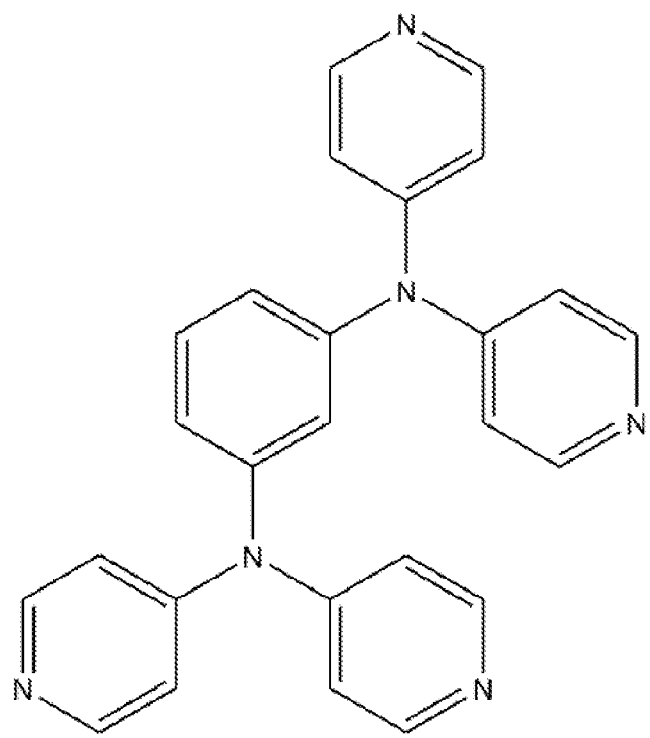
FIG. 15 is an illustration of an example ligand that may be incorporated into a coordination polymer.
Figure 16:
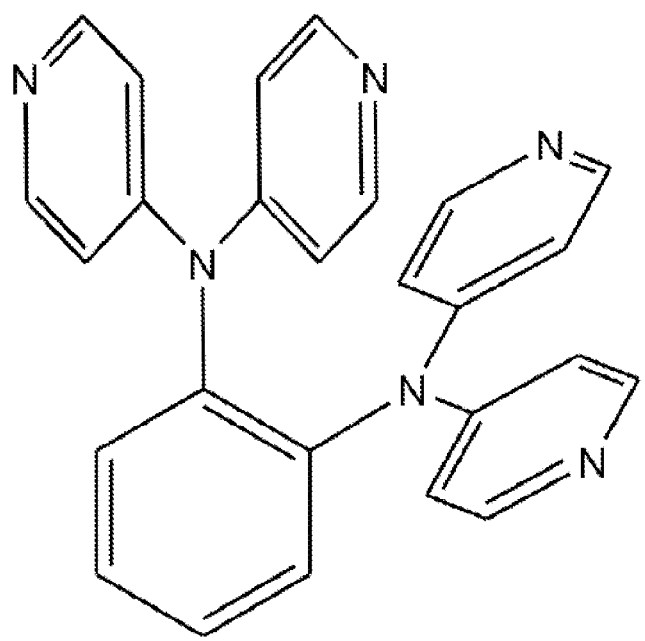
FIG. 16 is an illustration of an example ligand that may be incorporated into a coordination polymer.

A specific example of a monomer compound is N,N,N',N'-tetra(4-pyridyl)-1,4-phenylenediamine (as shown in FIG. 1). Another specific example of a monomer compound is N,N,N',N'-tetra(4-pyridyl)-1,3-phenylenediamine (as shown in FIG. 15). Another specific examples is N,N,N',N'-tetra(4-pyridyl)-1,2-phenylenediamine (as shown in FIG. 16).

Figure 4:
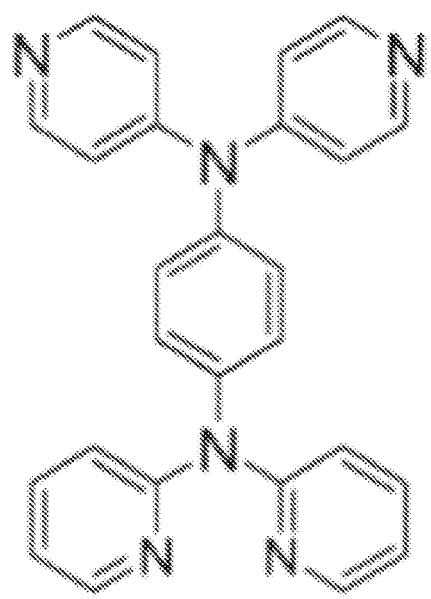
FIG. 4 is an illustration of an example ligand that may be incorporated into an oligomeric complex or a coordination polymer.
Figure 17:
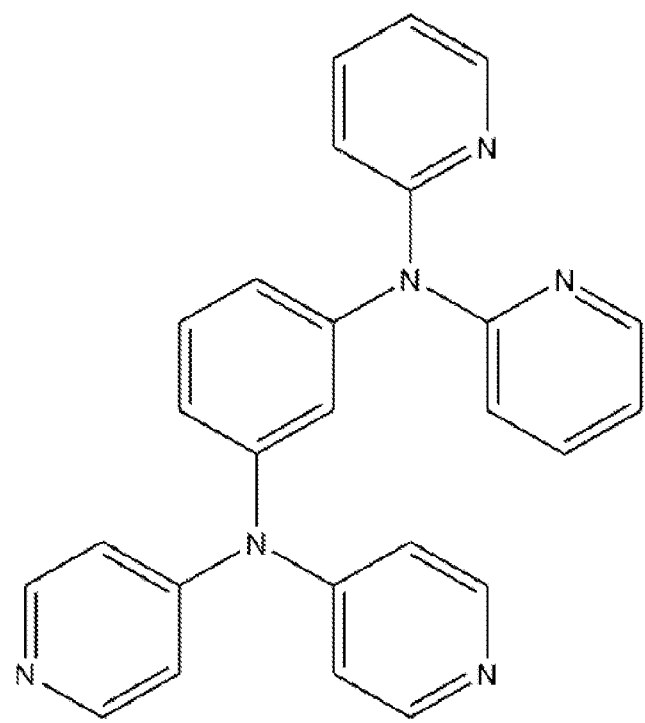
FIG. 17 is an illustration of an example ligand that may be incorporated into an oligomeric complex or a coordination polymer.
Figure 18:
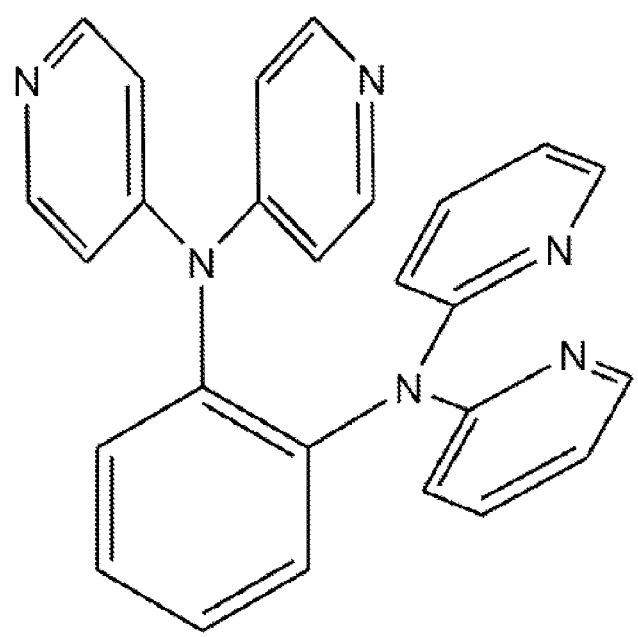
FIG. 18 is an illustration of an example ligand that may be incorporated into an oligomeric complex or a coordination polymer, all arranged in accordance with at least some embodiments of the present disclosure.
Figure 14:
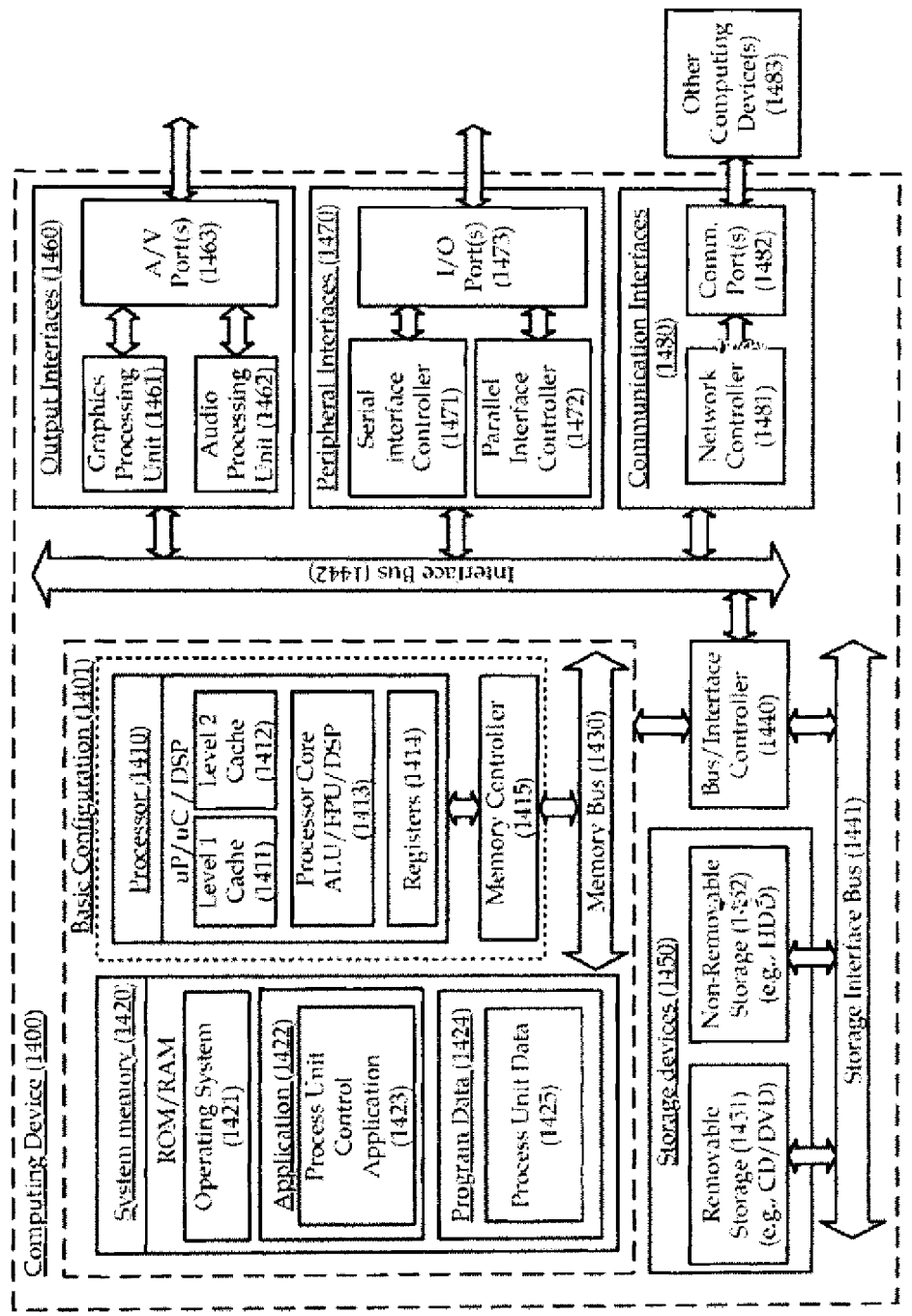

Another specific example of a monomer compound is N,N-di(2-pyridyl)-N',N'-di(4-pyridyl)-1,4-phenylenediamine (as shown in FIG. 4). Another specific compound is N,N-di(2-pyridyl)-N',N'-di(4-pyridyl)-1,3-phenylenediamine (as shown in FIG. 17). Another specific compound is N,N-di(2-pyridyl)-N',N'-di(4-pyridyl)-1,2-phenylenediamine (as shown in FIG. 18).

Oligomeric Complexes and Coordination Polymers

Oligomeric complexes and coordination polymers can contain two or more of one monomer compound ligands and two or more metal atoms. In general, coordination polymers may include a large number of ligands and metal atoms in the molecule. The term coordination polymer may comprise a subset of what may be termed complexes (in general, the meaning of "complex" may be the same as "coordination compounds"). In general, oligomeric complexes may include limited numbers of ligands and metal atoms. In another aspect, any one of the previously described monomer compounds can be complexed to one or more metal atoms. The metal atoms can generally be any metal atom suitable for binding to or complexing with at least one of the pyridinyl rings. In some examples, each monomer compound can be complexed with one, two, three, or four metal atoms. Each metal atom may be complexed with one, two, or more monomer compounds.

In some examples, the metal atom or atoms may include closed shell $d^{10}$ metal ions. In some examples, the metal atom or atoms may include zinc, cadmium, silver, or mercury. In some examples, the metal atom or atoms may include ionic zinc(II), ionic cadmium(II), ionic silver(I) or ionic mercury (II). The metal atom can be provided as a metal salt. Examples of metal salts include at least one zinc salt, at least one cadmium salt, at least one mercury salt, or mixtures thereof. As discussed, a variety of complexes may be formed using the discussed ligands and metal atoms. In general, those compounds or complexes may have a variety of uses in applications such as, for example, optoelectronic devices, optical devices, electronic devices, magnetic devices, molecular sensing devices, catalysis, gas adsorption, or the like. In some examples, those compounds may luminesce in the solid-state at room temperature. In some examples, the luminescent solid-state compound may be incorporated into device such as, for example, an optoelectronic device.

FIG. 1 is an illustration of an example monomer compound ligand that may be incorporated into a coordination polymer. Ligand may be N,N,N',N'-tetra(4-pyridyl)-1,4-phenylenediamine. As shown, ligand may include 4,4'-dpa (4,4'-dipyridylamine) as coordination moieties, such that two 4,4'-dpa units may be connected by a 1,4-phenylene unit. Therefore, ligand may be able to bridge up to four metal centers, which may provide for a variety of structures. As is further discussed herein, ligand may be structurally incorporated into a variety of complexes. In general, ligand may be designated $L^1$ in this description for the sake of clarity and ease of presentation.

FIG. 4 is an illustration of an example monomer compound ligand that may be incorporated into an oligomeric complex or a coordination polymer. Ligand may be N,N-di(2-pyridyl)-N',N'-di(4-pyridyl)-1,4-phenylenediamine. As shown, ligand may include 2,2'-dpa (2,2'-dipyridylamine) and 4,4'-dpa (4,4'-dipyridylamine) as coordination moieties, such that a 2,2'-dpa unit and a 4,4'-dpa unit may be connected by a 1,4-phenylene unit. In some examples, the chelating character of the 2,2'-dpa unit and the bridging character of the 4,4'-dpa unit may be combined, which may provide for a variety of structures. As is further discussed herein, ligand may be structurally incorporated into a variety oligomeric complexes or coordination polymers. In general, ligand may be designated $L^2$ in this description for the sake of clarity and ease of presentation.

Methods of Preparing Monomer Compounds

In another aspect, methods of preparing monomer compounds are described. Organic chemistry techniques can be used to connect the four pyridyl rings to the central linker portion to prepare the monomer compounds. Various catalysts and solvents can be used.

Different synthetic approaches may be used, depending on the degree of symmetry in the desired monomer compound. Routine separation techniques may be used when mixtures of monomer compounds or other materials are obtained.

Generally, the method can include contacting a first bipyridylamine, a second bipyridylamine, and a central linker portion having two reactive groups under conditions suitable to form the monomer compound ligand, wherein the central linker portion is a phenyl group, a biphenyl group, or a terphenyl group.

For monomer compounds that are symmetric relative to the central linker portion (such as in FIG. 1, where the top two pyridyl rings are the same as the bottom two pyridyl rings), a central linker portion with two reactive groups can be contacted with at least two molar equivalents of a bipyridylamine (first bipyrdyl $Py^1Py^2NH$ being the same as second bipyridyl $Py^3Py^4NH$) to obtain the desired monomer compound. In some examples, the central linker portion having two reactive groups can be a 1,4-dihalobenzene such as 1,4-dibromobenzene. In some examples, the central linker portion can be 1,4-diiodobenzene. In some examples, the central linker portion having two reactive groups can be a dihalobiphenyl such as dibromobiphenyl. In some examples, the central linker portion can be diiodoiphenyl. In some examples, the central linker portion having two reactive groups can be a dihaloterphenyl such as dibromoterphenyl. In some examples, the central linker portion can be diiodoterphenyl. This is an example of a single-step synthesis. An alternative approach would be a two-step "stepwise" synthesis, where the central linker portion is first connected to two pyridinyl rings, and then subsequently connected to two additional pyridinyl rings.

For monomer compounds that are asymmetric relative to the central linker portion (such as in FIG. 4, where the top two pyridinyl rings are different from the bottom two pyridinyl rings), a central linker portion can be contacted with at least one molar equivalent of a first bipyridinylamine ($Py^3Py^4NH$) to obtain an intermediate compound. The intermediate compound can be contacted with at least one molar equivalent of a second bipyridinylamine ($Py^3Py^4NH$) to obtain the desired monomer compound. This is an example of a two-step "stepwise" synthesis. An alternative approach would be a one-step synthesis, where the central linker portion is simultaneously contacted with a mixture of the first bipyridinylamine ($Py^1Py^2NH$) and the second bipyridinylamine ($Py^3Py^4NH$) to obtain the desired monomer compound. In this one-step synthesis, it is likely that a mixture of the desired monomer compound and other undesired compounds would be obtained. The desired compound could be easily separated from the undesired compounds using routine separation methods.

Figure 2:
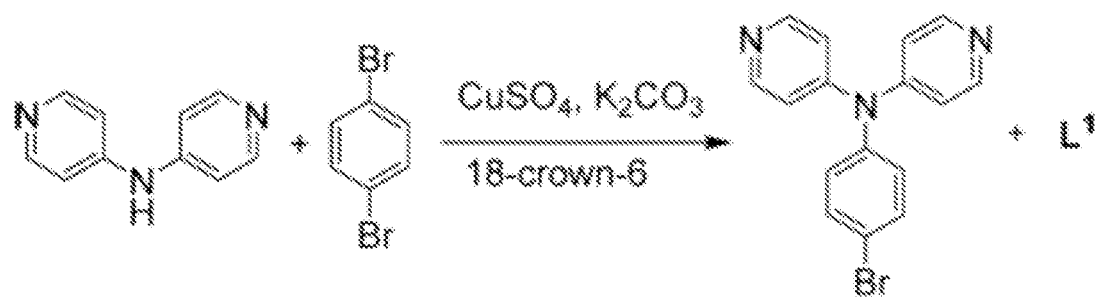
FIG. 2 is an illustration of an example chemical reaction for producing a ligand.

FIG. 2 is an illustration of a specific example chemical reaction for producing ligand $L^1$. As shown, in some examples, 4,4'-dipyridylamine and 1,4-dibromobenzene may react in the presence of cupric sulfate ($CuSO_4$), 18-crown-6 and anhydrous potassium carbonate ($K_2CO_3$) to form the desired ligand (labeled $L^1$ in FIG. 2) and (4-bromophenyl)-di(4-pyridyl)amine (resulting from incomplete reaction). In some examples, at least a portion of the chemical reaction may take place in the presence of at least one solvent such as a diphenyl ether solvent. In general, the chemical reaction may be performed in batch processing or continuous processing. In some examples, the chemical reaction may be operated in conjunction with one or more separation and purification techniques to yield desired ligand $L^1$.

FIG. 3 is an illustration of a flow chart of a specific example method for producing desired ligand $L^1$. Method 300 may include one or more functions, operations or actions as illustrated by one or more of blocks 310, 320, 330 and/or 340. In some examples, method 300 may be implemented using a process system as is further discussed herein and/or under the control of a computer system, as is discussed further herein. Processing for method 300 may begin at block 310.

At block 310, "Heat a Mixture of 4,4'-dipyridylamine, 1,4-dibromobenzene, cupric sulfate, anhydrous potassium carbonate, 18-crown-6, and diphenyl ether", a mixture of the listed components may be heated. In general, any suitable amounts of the listed components may be heated for any suitable temperature and duration to yield desired ligand $L^1$. Also, any suitable techniques may be used to heat or stir the components. In some examples, the mixture may be heated at a temperature of about 200° C. for about 3 days. In some examples, the processing may be performed using batch techniques such that the reaction is performed in a single vessel and the materials may be removed as a whole at completion of the reaction. In some examples, the processing may be performed using continuous processing techniques such that raw materials may be fed substantially continuously into a reactor and finished materials may be removed substantially continuously from the reactor. Processing may continue at block 320.

As discussed with respect to block 310, a mixture of 4,4-dipyridylamine, 1,4-dibromobenzene, cupric sulfate, anhydrous potassium carbonate, 18-crown-6, and diphenyl ether may be heated. In general, the mixture may be heated to any suitable temperature. In some examples, the mixture may be heated at a temperature of about 200° C. In some examples, the mixture may be heated at a temperature in the range of about 150 to 200° C. In some examples, the mixture may be heated at a temperature of about 200 to 250° C. In general, the mixture may be heated for any suitable duration. In some examples, the mixture may be heated for a duration of about 3 days. In some examples, the mixture may be heated for a duration in the range of about 50 to 75 hours. In some examples, the mixture may be stirred during heating. In general, any amounts of the listed components may be used. In some examples, the weight percentages of the 4,4'-dipyridylamine, 1,4-dibromobenzene, cupric sulfate, anhydrous potassium carbonate, and 18-crown-6 may be in the ranges of about 30 to 35 wt % 4,4'-dipyridylamine, 15 to 20 wt % 1,4-dibromobenzene, 5 to 10 wt % cupric sulfate, 35 to 40 wt % anhydrous potassium carbonate, and 0.5 to 5 wt % 18-crown-6. In some examples, the diphenyl ether may be considered a solvent and the amount of diphenyl ether in the mixture may provide substantial wetting, dissolution or emulsion of the other components. In some examples, the combined weight of the other components may be about 12.5 grams and the volume of diphenyl ether may be about 35 milliliters. In some examples, the ratio of the weight of combined components (in grams) to the volume of diphenyl ether (in milliliters) may be in the range of about 0.25 to 0.5. In some examples, at some point during the heating of the mixture, additional 1,4-dibromobenzene may be added.

At block 320, "Cool the Mixture", the mixture may be cooled such that at least a portion of the mixture includes a solid that includes a ligand. In some examples, the formed ligand may include N,N,N',N'-tetra(4-pyridyl)-1,4-phenylenediamine, as shown in FIGS. 1 and 2. In general, the mixture may be cooled using any suitable technique or techniques. In some examples, the mixture may be cooled to room temperature or to below room temperature. In some examples, the mixture may be cooled using refrigeration. In some examples, the mixture may be cooled using a cooling jacket that may flow cool water (or other cooling liquid) in heat removal contact with the mixture. In some examples, the cooling may be performed using batch techniques such that a batch of material may be cooled from the reaction temperature down to a cooled temperature. In other examples, the cooling may be done using continuous processing techniques such that reaction temperature material may be fed substantially continuously for cooling and cooled material may be removed from the processed material substantially continuously. Processing may continue at block 330.

At block 330, "Dissolve the Solid Into a Solvent", the separated solid may be dissolved into a solvent. In general, any suitable solvent or solvents may be used that may provide dissolution of the solid and opportunity for separation or purification of the ligand. In some examples, the solvent may include dichloromethane and water. In some examples, the solid may be dissolved using batch techniques such that the solid and solvent may be combined in a batch reactor, dissolved and removed upon completion. In some examples, continuous processing techniques may be used such that the solid and the solvent or solvents may be added to a processing unit substantially continuously and solid dissolved in solvent product may be removed from the processing unit substantially continuously. Processing may continue at block 340.

At block 340, "Purify the Ligand from the Solvent", the ligand may be purified from the solvent. In general, any suitable technique or techniques may be used to purify the ligand from the solvent. In some examples, the purification may include washing an organic phase of the solvent with distilled water and drying with sodium sulfate. In some examples, washing the organic phase with distilled water may include washing the organic phase to a neutral pH. In some examples, after washing with distilled water and drying with sodium sulfate, the ligand may be separated out using a silica gel column. In some examples, separating the ligand may include separating the ligand from a solid form of (4-bromophenyl)-di(4-pyridyl)amine. In some examples, the ligand may be purified using batch techniques such that the ligand may be purified in a batch reactor and removed upon completion. In some examples, continuous processing techniques may be used such that the dissolved solid in solvent may be added to a separation unit substantially continuously and the purified ligand may be removed from the processing unit substantially continuously.

Figure 5:
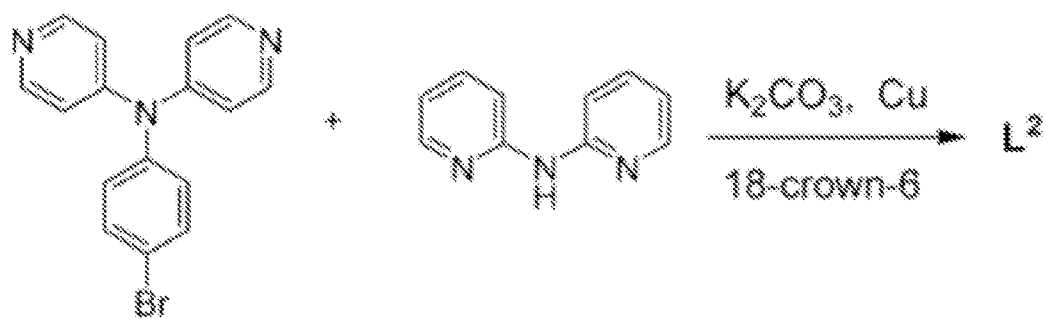
FIG. 5 is an illustration of an example chemical reaction for producing a ligand.

FIG. 5 is an illustration of an example chemical reaction for producing monomer compound ligand $L^2$. As shown, (4-bromophenyl)-di(4-pyridyl)amine and 2,2-dipyridylamine may react in the presence of anhydrous potassium carbonate, bronze powder, and 18-crown-6 to form ligand $L^2$. In some examples, at least a portion of the chemical reaction may take place in a dimethylformamide (DMF) solvent. In general, the chemical reaction may be performed in batch processing or continuous processing. In some examples, the chemical reaction may be operated in conjunction with one or more separation and purification techniques to yield monomer compound ligand $L^2$.

Figure 6:
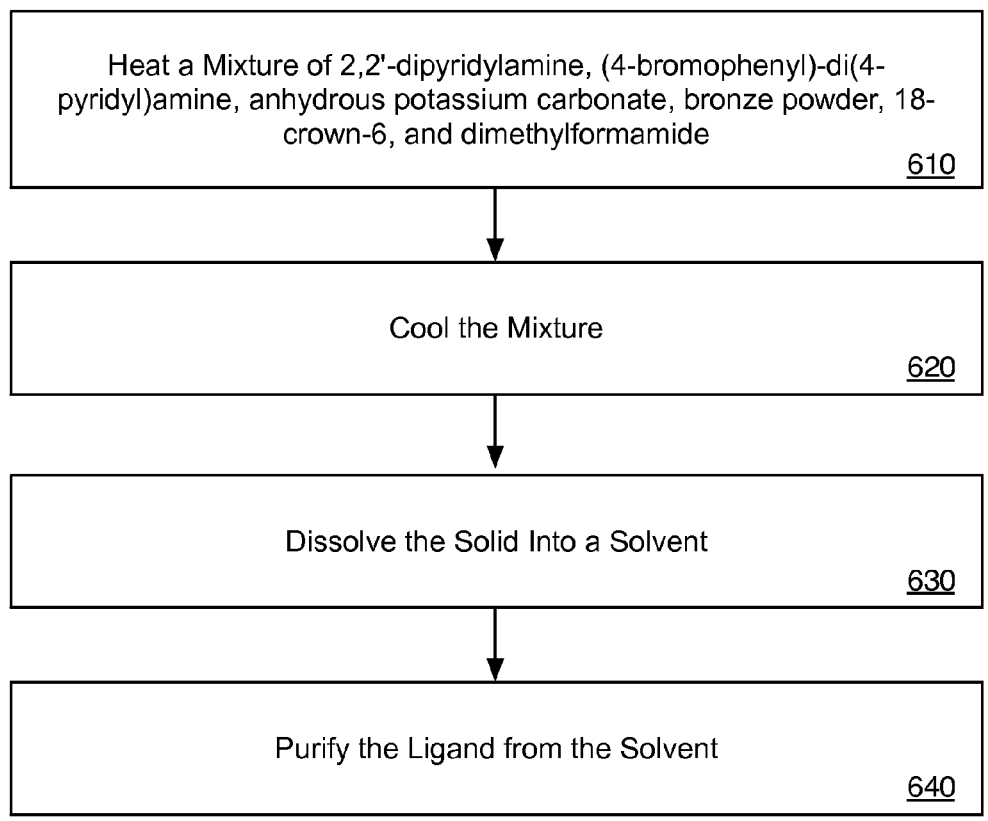
FIG. 6 is an illustration of a flow chart of an example method for producing a ligand.

FIG. 6 is an illustration of a flow chart of an example method 600 for producing ligand $L^2$. Method 600 may include one or more functions, operations or actions as illustrated by one or more of blocks 610, 620, 630 and/or 640. In some examples, method 600 may be implemented using a process system as is further discussed herein and/or under the control of a computer system, as is discussed further herein. Processing for method 600 may begin at block 610.

At block 610, "Heat a Mixture of 2,2'-dipyridylamine, (4-bromophenyl)-di(4-pyridyl)amine, anhydrous potassium carbonate, bronze powder, 18-crown-6, and dimethylformamide", a mixture of the listed components may be heated. In general, any suitable amounts of the listed components may be heated for at any suitable temperature and duration to yield ligand $L^2$. Also, any suitable techniques may be used to heat or stir the components. In some examples, the mixture may be heated at a temperature of about 145° C. for about 30 hours under a nitrogen environment. In some examples, the processing may be performed using batch techniques such that the reaction is performed in a single vessel and the materials are removed as whole at completion of the reaction. In some examples, the processing may be performed using continuous processing techniques such that raw materials may be fed substantially continuously into a reactor and finished materials may be removed substantially continuously from the reactor. Processing may continue at block 620.

As discussed with respect to block 610, a mixture of 2,2'-dipyridylamine, (4-bromophenyl)-di(4-pyridyl)amine, anhydrous potassium carbonate, bronze powder, 18-crown-6, and dimethylformamide of may be heated. In general, the mixture may be heated to any suitable temperature. In some examples, the mixture may be heated at a temperature of about 145° C. In some examples, the mixture may be heated at a temperature in the range of about 100 to 150° C. In some examples, the mixture may be heated at a temperature in the range of about 140 to 200° C. In some examples, the mixture may be heated for a duration of about 30 hours. In some examples, the mixture may be heated for a duration in the range of about 20 to 30 hours. In some examples, the mixture may be heated for a duration in the range of about 30 to 40 hours. In some examples, the mixture may be stirred during heating. In general, any suitable amounts of the listed components may be used. In some examples, the weight percentages of the 2,2'-dipyridylamine, (4-bromophenyl)-di(4-pyridyl)amine, anhydrous potassium carbonate, bronze powder, and 18-crown-6 may be in the ranges of about 30 to 35 wt % 2,20-dipyridylamine, 10 to 20 wt % (4-bromophenyl)-di(4-pyridyl)amine, 10 to 20 wt % anhydrous potassium carbonate, 25 to 35 wt % bronze powder, and 0.5 to 5 wt % 18-crown-6. In some examples, the dimethylformamide may be considered a solvent and the amount of dimethylformamide in the mixture may provide substantial wetting, dissolution or emulsion of the other components. In some examples, the combined weight of the other components may be about 15.5 grams and the volume of dimethylformamide may be about 125 milliliters. In some examples, the ratio of the weight of combined components (in grams) to the volume of dimethylformamide (in milliliters) may be in the range of about 0.05 to about 0.2. In some examples, the heating may be done under a nitrogen environment.

At block 620, "Cool the Mixture", the mixture may be cooled such that at least a portion of the mixture includes a solid that includes a ligand. In some examples, the formed ligand may include N,N-di(2-pyridyl)-N',N'-di(4-pyridyl)-1,4-phenylenediamine, as shown in FIGS. 4 and 5. In general, the mixture may be cooled using any suitable technique or techniques. In some examples, the mixture may be cooled to room temperature or to below room temperature. In some examples, the mixture may be cooled using refrigeration. In some examples, the mixture may be cooled using a cooling jacket that may flow cool water (or other cooling liquid) in heat removal contact with the mixture. In some examples, the cooling may be performed using batch techniques such that a batch of material may be cooled from the reaction temperature down to a cooled temperature. In other examples, the cooling may be done using continuous processing techniques such that reaction temperature material may be fed substantially continuously for cooling and cooled material may be removed from the processing substantially continuously. Processing may continue at block 630.

At block 630, "Dissolve the Solid Into a Solvent", the separated solid may be dissolved into a solvent. In general, any suitable solvent or solvents may be used that may provide dissolution of the solid and opportunity for separation or purification of the ligand. In some examples, the solvent may include dichloromethane and water. In some examples, the solid may be dissolved using batch techniques such that the solid and solvent may be combined in a batch reactor, dissolved and removed upon completion. In some examples, continuous processing techniques may be used such that the solid and the solvent or solvents may be added to a processing unit substantially continuously and completed solid dissolved in solvent product may be removed from the processing unit substantially continuously. Processing may continue at block 640.

At block 640, "Purify the Ligand from the Solvent", the ligand may be purified from the solvent. In general, any suitable technique or techniques may be used to purify the ligand from the solvent. In some examples, the purification may include washing an organic phase of the solvent with distilled water and drying with sodium sulfate. In some examples, washing the organic phase with distilled water may include washing the organic phase to a neutral pH. In some examples, after washing with distilled water and drying with sodium sulfate, the ligand may be separated out using a silica gel column. In some examples, the ligand may be purified using batch techniques such that the ligand may be purified in a batch reactor and removed upon completion. In some examples, continuous processing techniques may be used such that the dissolved solid in solvent may be added to a separation unit substantially continuously and the purified ligand may be removed from the processing unit substantially continuously.

Coordination Modes and Polymers

Figure 7:
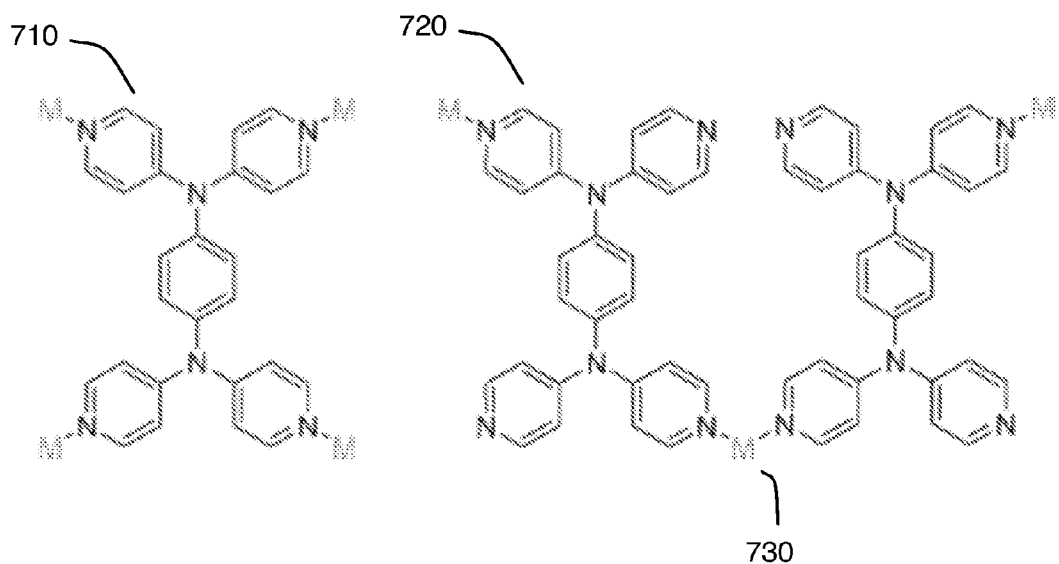
FIG. 7 is an illustration of example coordination modes for a ligand.
Figure 8A:
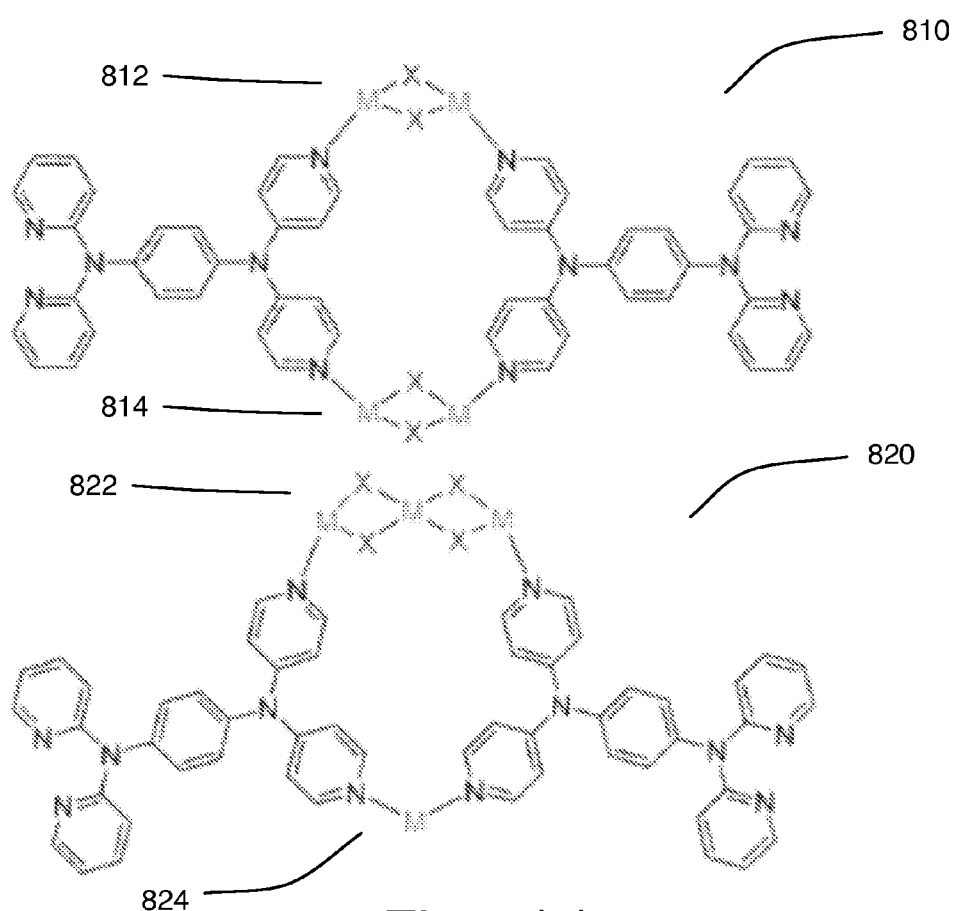
FIG. 8 is an illustration of example coordination modes for a ligand.
Figure 8B:
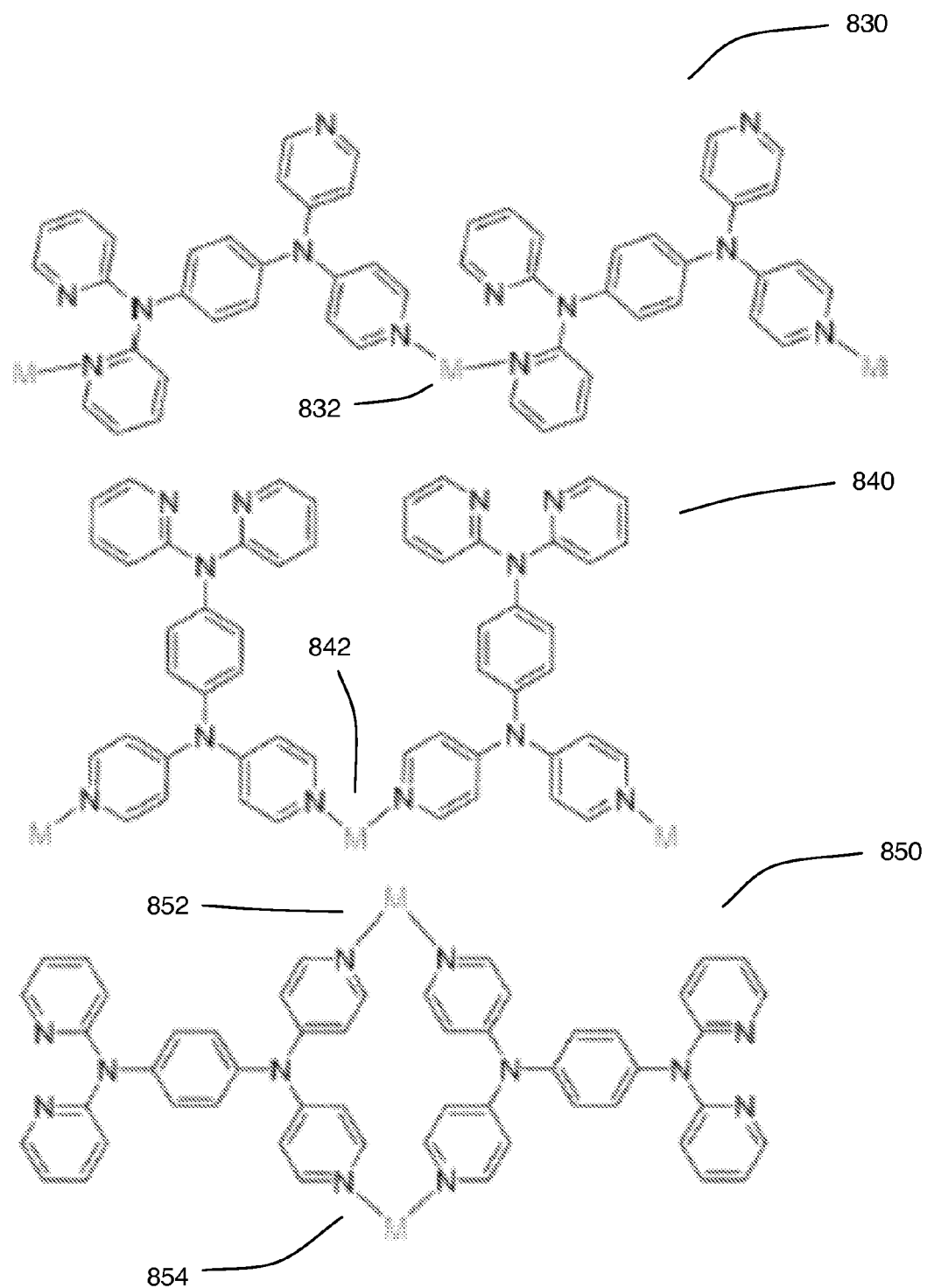

While not intended to be bound by theory, FIGS. 7, 8a, and 8b illustrate possible configurations of one or more ligands and one or more metal atoms.

FIG. 7 is an illustration of example coordination modes for ligand $L^1$ (N,N,N',N'-tetra(4-pyridyl)-1,4-phenylenediamine). As shown, in some examples, ligand $L^1$ may be incorporated in a coordination mode 710 or a coordination mode 720. In some examples, coordination mode 710 may include ligand $L^1$ incorporated with four metal atoms (labeled M in FIG. 7). In some examples, ligand $L^1$ may be incorporated in coordination mode 710 with one, two or three metal atoms. In some examples, the metal atoms may be structurally incorporated with ligand $L^1$ at one or more locations corresponding to the nitrogen in a pyridyl group of ligand $L^1$. In some examples, the metal atoms may by ionic zinc(II). In some examples, the metal atoms may be ionic cadmium(II). In some examples, the metal atoms may be ionic mercury(II). In some examples, the metal atoms may be ionic silver(I). In some examples, the metal atoms may be the same. In some examples, they may be different. In various examples, the metal atoms may be chosen from ionic zinc(II), ionic cadmium(II), ionic silver(I), or ionic mercury(II) in any combination. In some examples, some or all of the metal atoms in coordination mode 710 may further coordinate to other ligands to yield an extended structure.

In some examples, coordination mode 720 may include two ligands $L^1$ incorporated such that they may be bound together by metal atom 730, which may be located between a nitrogen in a pyridyl group of a ligand $L^1$ and a nitrogen in a pyridyl group of another ligand $L^1$. In some examples, coordination mode 720 may include two ligands $L^1$ structurally incorporated with three metal atoms (labeled M in FIG. 7). In some examples, ligands $L^1$ may be incorporated in coordination mode 720 with one, two or three metal atoms. In some examples, the metal atoms may by ionic zinc(II). In some examples, the metal atoms may be ionic cadmium(II). In some examples, the metal atoms may be ionic mercury(II). In some examples, the metal atoms may be ionic silver(I). In some examples, the metal atoms may be the same. In some examples, they may be different. In various examples, the metal atoms may be chosen from ionic zinc(II), ionic cadmium(II), ionic silver(I) or ionic mercury(II) in any combination. In some examples, the metal atoms at the outer ends of coordination mode 720 may further coordinate to other ligands to yield an extended structure.

While not shown in FIG. 7, one or more other atoms or molecules may be present (such as shown in FIG. 8a). The other atoms or molecules "X" can be anionic. The other atoms "X" may include, for example, chlorine, bromine, iodine, or the like in any suitable combination.

FIG. 8 (including FIGS. 8(a) and 8(b)) is an illustration of example coordination modes for ligand $L^2$ (N,N-di(2-pyridyl)-N',N'-di(4-pyridyl)-1,4-phenylenediamine). As shown, in some examples, ligand $L^2$ may be incorporated in one of coordination modes 810, 820, 830, 840 or 850. In some examples, coordination mode 810 may include two $L^2$ ligands incorporated such that they may be bound together at locations 812, 814. Location 812 may correspond to a nitrogen in a pyridyl group of a first $L^2$ ligand and a nitrogen in pyridyl group of a second $L^2$ ligand. Location 814 may correspond to a second nitrogen in a second pyridyl group of the first $L^2$ ligand and a second nitrogen in a second pyridyl group of the second $L^2$ ligand. In some examples, the $L^2$ ligands may be incorporated in coordination mode 810 with four metal atoms (labeled M in FIG. 8(a)) and four other atoms or molecules (labeled "X" in FIG. 8(a)). The other atoms or molecules "X" can be anionic. In some examples, the metal atoms may by ionic zinc(II). In some examples, the metal atoms may be ionic cadmium(II). In some examples, the metal atoms may be ionic mercury(II). In some examples, the metal atoms may be ionic silver(II). In some examples, the metal atoms may be the same. In some examples, they may be different. In various examples, the metal atoms may be chosen from ionic zinc(II), ionic cadmium(II), ionic silver(I) or ionic mercury(II) in any combination. The other atoms "X" may include, for example, chlorine, bromine, iodine, or the like in any suitable combination.

In some examples, coordination mode 820 may include two $L^2$ ligands incorporated such that they may be bound together at locations 822, 824. Location 822 may correspond to a nitrogen in a pyridyl group of a first $L^2$ ligand and a nitrogen in pyridyl group of a second $L^2$ ligand. Location 824 may correspond to a second nitrogen in a second pyridyl group of the first $L^2$ ligand and a second nitrogen in a second pyridyl group of the second $L^2$ ligand. In some examples, the $L^2$ ligands may be incorporated in coordination mode 820 with four metal atoms (labeled M in FIG. 8(a)) and four other atoms or molecules (labeled X in FIG. 8(a)). In some examples, the metal atoms may by ionic zinc(II). In some examples, the metal atoms may be ionic cadmium(II). In some examples, the metal atoms may be ionic mercury(II). In some examples, the metal atoms may be ionic silver(II). In some examples, the metal atoms may be the same. In some examples, they may be different. In various examples, the metal atoms may be chosen from ionic zinc(II), ionic cadmium(II), ionic silver or ionic mercury(II) in any combination. The other atoms may include, for example, chlorine, bromine, iodine, or the like in any suitable combination.

In some examples, coordination mode 830 may include two $L^2$ ligands incorporated such that they may be bound together metal atom 832, which may be located between a nitrogen in a pyridyl group of a $L^2$ ligand and a nitrogen in a pyridyl group of another $L^2$ ligand. In some examples, coordination mode 830 may include two ligands $L^2$ structurally incorporated with three metal atoms (labeled M in FIG. 8(b)). In some examples, the $L^2$ ligands may be incorporated in coordination mode 830 with one, two or three metal atoms. In some examples, the metal atoms may by ionic zinc(II). In some examples, the metal atoms may be ionic cadmium(II). In some examples, the metal atoms may be ionic mercury(II). In some examples, the metal atoms may be ionic silver(II). In some examples, the metal atoms may be the same. In some examples, they may be different. In various examples, the metal atoms may be chosen from ionic zinc(II), ionic cadmium(II), ionic silver(I) or ionic mercury(II) in any combination. In some examples, the metal atoms at the outer ends of coordination mode 830 may further coordinate to other ligands to yield an extended structure.

In some examples, coordination mode 840 may include two $L^2$ ligands incorporated such that they may be bound together by metal atom 842, which may be located between a nitrogen in a pyridyl group of a $L^2$ ligand and a nitrogen in a pyridyl group of another $L^2$ ligand. In some examples, coordination mode 840 may include two ligands $L^2$ structurally incorporated with three metal atoms (labeled M in FIG. 8(b)). In some examples, the $L^2$ ligands may be incorporated in coordination mode 840 with one, two or three metal atoms. In some examples, the metal atoms may by ionic zinc(II). In some examples, the metal atoms may be ionic cadmium(II). In some examples, the metal atoms may be ionic mercury(II). In some examples, the metal atoms may be ionic silver(II). In some examples, the metal atoms may be the same. In some examples, they may be different. In various examples, the metal atoms may be chosen from ionic zinc(II), ionic cadmium(II), ionic silver(I) or ionic mercury(II) in any combination. In some examples, the metal atoms at the outer ends of coordination mode 840 may further coordinate to other ligands to yield an extended structure.

In some examples, coordination mode 850 may include two $L^2$ ligands incorporated such that they may be bound together at locations 852, 854. Location 852 may correspond to a nitrogen in a pyridyl group of a first $L^2$ ligand and a nitrogen in pyridyl group of a second $L^2$ ligand. Location 854 may correspond to a second nitrogen in a second pyridyl group of the first $L^2$ ligand and a second nitrogen in a second pyridyl group of the second $L^2$ ligand. In some examples, the $L^2$ ligands may be incorporated in coordination mode 850 with two metal atoms (labeled M in FIG. 8(a)). In some examples, the metal atoms may by ionic zinc(II). In some examples, the metal atoms may be ionic cadmium(II). In some examples, the metal atoms may be ionic mercury(II). In some examples, the metal atoms may be ionic silver(II). In some examples, the metal atoms may be the same. In some examples, they may be different. In various examples, the metal atoms may be chosen from ionic zinc(II), ionic cadmium(II), ionic silver(I) or ionic mercury(II) in any combination.

As discussed, in various examples, the $L^1$ and $L^2$ ligands may be incorporated with metal atoms or ions to form coordination polymers or oligomeric complexes. The ligands may be incorporated into a wide range of coordination polymers or oligomeric complexes that may have a wide range of advantageous characteristics. Discussed immediately below are example coordination polymers and oligomeric complexes and example methods for forming the example coordination polymers and oligomeric complexes. As discussed, herein ligand N,N,N',N'-tetra(4-pyridyl)-1,4-phenylenediamine may be designated $L^1$ and ligand N,N-di(2-pyridyl)-N',N'-di(4-pyridyl)-1,4-phenylenediamine may be designated $L^2$.

Oligomeric complexes and coordination polymers can contain two or more of one monomer compound ligand. For example, an oligomeric complex or a coordination polymer can comprise two or more $L^1$ monomer compound ligands or two or more $L^2$ monomer compound ligands.

In some examples, the coordination polymer may be $Zn_2L^1Cl_4$. In some examples, the coordination polymer $Zn_2L^1Cl_4$ may be formed by mixing and heating the $L^1$ ligand and zinc chloride ($ZnCl_2$) in methanol for a duration in the range of about 2 to 4 hours. In some examples, the mixture may be cooled, washed with methanol and dried. In some examples, the resultant coordination polymer $Zn_2L^1Cl_4$ may be a yellowish microcrystalline precipitate.

In some examples, the coordination polymer may be $Zn_2L^1Br_4.MeOH$. In some examples, the coordination polymer $Zn_2L^1Br_4.MeOH$ may be formed by mixing and heating the $L^1$ ligand and zinc bromide ($ZnBr_2$) in methanol for a duration in the range of about 2 to 4 hours. In some examples, the mixture may be cooled, washed with methanol and dried. In some examples, the resultant coordination polymer $Zn_2L^1Br_4.MeOH$ may be a yellowish microcrystalline precipitate.

In some examples, the coordination polymer may be $Zn_2L^1I_4$. In some examples, the coordination polymer $Zn_2L^1I_4$ may be formed by mixing and heating the $L^1$ ligand and zinc iodide ($ZnI_2$) in methanol for a duration in the range of about 2 to 4 hours. In some examples, the mixture may be cooled, washed with methanol and dried. In some examples, the resultant coordination polymer $Zn_2L^1I_4$ may be a yellowish microcrystalline precipitate.

In some examples, the coordination polymer may be $[CdL^1Cl_2]_n.nH_2O$. The value n is an integer of two or more. In some examples, the coordination polymer $[CdL^1Cl_2]_n.nH_2O$ may be formed by mixing and heating $L^1$, $Cd(NO_3)2.4H2O$ and sodium chloride (NaCl) in dimethylsulfoxide (DMSO), dimethylformamide (DMF), water and methanol to a temperature in the range of about 100 to 140° C. for a duration in the range of about 80 to 100 hours. In some examples, the mixture may be cooled, washed with methanol and dried. In some examples, the resultant coordination polymer $[CdL^1Cl_2]_n.nH_2O$ may be a clear crystal.

In some examples, the coordination polymer may be $[CdL^1Br_2].7.5H_2O$. In some examples, the coordination polymer $[CdL^1Br_2].7.5H_2O$ may be formed by mixing and heating the $L^1$ ligand, potassium bromide (KBr) and $Cd(NO_3)_2.4H_2O$ in methanol for a duration in the range of about 2 to 4 hours. In some examples, the mixture may be cooled, washed with methanol and dried. In some examples, the resultant coordination polymer $[CdL^1Br_2].7.5H_2O$ may be a yellowish microcrystalline precipitate.

In some examples, the coordination polymer may be $[CdL^1I_2]_n$. The value n is an integer of two or more. In some examples, the coordination polymer $[CdL^1I_2]_n$ may be formed by mixing and heating $L^1$, $Cd(NO_3)_2 \cdot 4H_2O$ and potassium iodide (KI) in dimethyl sulfoxide (DMSO), dimethylformamide (DMF), water and methanol to a temperature in the range of about 100 to 140° C. for a duration in the range of about 80 to 100 hours. In some examples, the mixture may be cooled, washed with methanol and dried. In some examples, the resultant coordination polymer $[CdL^1I_2]_n$ may be a clear crystal.

In some examples, the coordination polymer may be $[HgL^1Cl_2]_n$. The value n is an integer of two or more. In some examples, the coordination polymer $[HgL^1Cl_2]_n$ may be formed by mixing $L^1$ and mercury(II) chloride ($HgCl_2$) in dimethyl sulfoxide (DMSO), dimethylformamide (DMF) and water, refluxing the mixture in air for a duration in the range of about 2 to 4 hours, and heating the mixture at a temperature in the range of about 100 to 140° C. for a duration in the range of about 80 to 100 hours. In some examples, the coordination polymer $[HgL^1Cl_2]_n$ may be a clear crystal.

In some examples, the coordination polymer may be $[HgL^1Cl_2]_n$. The value n is an integer of two or more. In some examples, the coordination polymer $[HgL^1Br_2]_n$ may be formed by mixing and heating $L^1$, $Hg(NO_3)_2 \cdot \frac{1}{2}H_2O$ and potassium bromide (KBr) in dimethyl sulfoxide (DMSO), dimethylformamide (DMF), water and methanol to a temperature in the range of about 100 to 140° C. for a duration in the range of about 80 to 100 hours. In some examples, the mixture may be cooled, washed with methanol and dried. In some examples, the resultant coordination polymer $[HgL^1Br_2]_n$ may be a clear crystal.

In some examples, the coordination polymer may be $HgL^1I_2$. The value n is an integer of two or more. In some examples, the coordination polymer $HgL^1I_2$ may be formed by mixing and heating the $L^1$ ligand and mercury(II) chloride ($HgL^1I_2$) in methanol for a duration in the range of about 2 to 4 hours. In some examples, the mixture may be cooled, washed with methanol and dried. In some examples, the resultant coordination polymer $HgL^1I_2$ may be a yellowish microcrystalline precipitate.

In some examples, the coordination polymer may be $ZnL^2Cl_2$. In some examples, the coordination polymer $ZnL^2Cl_2$ may be formed by heating a mixture of the $L^2$ ligand and zinc chloride ($ZnCl_2$) in methanol, refluxing the mixture in air for a duration in the range of about 2 to 4 hours and slowly cooling the mixture to room temperature. In some examples, the resultant coordination polymer $ZnL^2Cl_2$ may be a yellowish microcrystalline precipitate.

In some examples, the coordination polymer may be $ZnL^2Br_2$. In some examples, the coordination polymer $ZnL^2Br_2$ may be formed by heating a mixture of the $L^2$ ligand and zinc bromide ($ZnBr_2$) in methanol, refluxing the mixture in air for a duration in the range of about 2 to 4 hours and slowly cooling the mixture to room temperature. In some examples, the resultant coordination polymer $ZnL^2Br_2$ may be a yellowish microcrystalline precipitate.

In some examples, the coordination polymer may be $ZnL^2I_2$. In some examples, the coordination polymer $ZnL^2I_2$ may be formed by heating a mixture of the $L^2$ ligand and zinc iodide ($ZnI_2$) in methanol, refluxing the mixture in air for a duration in the range of about 2 to 4 hours and slowly cooling the mixture to room temperature. In some examples, the resultant coordination polymer $ZnL^2I_2$ may be a clear crystal.

In some examples, the coordination polymer may be $[Cd(L^2)_4Cl_8]_n \cdot 2nDMF$. The value n is an integer of two or more. In some examples, the coordination polymer $[Cd(L^2)_4Cl_8]_n \cdot 2nDMF$ may be formed by mixing and heating $L^2$, $Cd(NO_3)_2 \cdot 4H_2O$ and sodium chloride (NaCl) in dimethyl sulfoxide (DMSO), dimethylformamide (DMF), water and methanol to a temperature in the range of about 100 to 140° C. for a duration in the range of about 80 to 100 hours. In some examples, the mixture may be cooled, washed with methanol and dried. In some examples, the resultant coordination polymer $[Cd(L^2)_4Cl_8]_n \cdot 2nDMF$ may be a clear crystal.

In some examples, the coordination polymer may be $[CdL^2Br_2]_n$. The value n is an integer of two or more. In some examples, the coordination polymer $[CdL^2Br_2]_n$ may be formed by heating a mixture of $L^2$, $Cd(NO_3)_2 \cdot 4H_2O$ and potassium bromide (KBr) in dimethyl sulfoxide (DMSO), dimethylformamide (DMF), water at a temperature in the range of about 100 to 140° C. for a duration in the range of about 80 to 100 hours, and cooling the mixture to room temperature. In some examples, the resultant coordination polymer $[CdL^2Br_2]_n$ may be a clear crystal.

In some examples, the coordination polymer may be $[CdL^2I_2]_n$. The value n is an integer of two or more. In some examples, the coordination polymer $[CdL^2I_2]_n$ may be formed by heating a mixture of $L^2$, $Cd(NO_3)_2 \cdot 4H_2O$ and potassium iodide (KI) in dimethyl sulfoxide (DMSO), dimethylformamide (DMF), water at a temperature in the range of about 100 to 140° C. for a duration in the range of about 80 to 100 hours, and cooling the mixture to room temperature. In some examples, the resultant coordination polymer $[CdL^2I_2]_n$ may be a clear crystal.

In some examples, the coordination polymer may be $[HgL^2Cl_2]_n \cdot 0.5nDMF$. The value n is an integer of two or more. In some examples, the coordination polymer $[HgL^2Cl_2]_n \cdot 0.5nDMF$ may be formed by mixing $L^2$ and mercury(II) chloride ($HgCl_2$) in dimethylsulfoxide (DMSO), dimethylformamide (DMF) and water, refluxing the mixture in air for a duration in the range of about 2 to 4 hours, and heating the mixture at a temperature in the range of about 100 to 140° C. for a duration in the range of about 80 to 100 hours. In some examples, the coordination polymer $[HgL^2Cl_2]_n \cdot 0.5nDMF$ may be a clear crystal.

In some examples, the oligomeric complex may be $[Hg_2(L^2)_2Br_4] \cdot H_2O$. In some examples, the oligomeric complex $[Hg_2(L^2)_2Br_4] \cdot H_2O$ may be formed by heating a mixture of $L^2$, $Hg(NO_3)_2 \cdot \frac{1}{2}H_2O$ and potassium bromide (KBr) in dimethyl sulfoxide (DMSO), dimethylformamide (DMF), water at a temperature in the range of about 100 to 140° C. for a duration in the range of about 80 to 100 hours, and cooling the mixture to room temperature. In some examples, the resultant oligomeric complex $[Hg_2(L^2)_2Br_4] \cdot H_2O$ may be a clear crystal.

In some examples, the oligomeric complex may be $[Hg_2(L^2)_2I_4] \cdot H_2O$. In some examples, the oligomeric complex $[Hg_2(L^2)_2I_4] \cdot H_2O$ may be formed by heating a mixture of $L^2$, mercury iodide ($HgI_2$) in dimethyl sulfoxide (DMSO), dimethylformamide (DMF), water at a temperature in the range of about 100 to 140° C. for a duration in the range of about 80 to 100 hours, and cooling the mixture to room temperature. In some examples, the resultant oligomeric complex $[Hg_2(L^2)_2I_4] \cdot H_2O$ may be a clear crystal.

Photoluminescence Properties and Uses

As discussed, in some examples, the oligomeric complexes and coordination polymers discussed herein may be used in photoluminescent devices. In some examples, the oligomeric complexes and coordination polymers may photoluminesce in the solid state. In some examples, the oligomeric complexes and coordination polymers may photoluminesce in the solid state at room temperature. In some examples, the oligomeric complexes and coordination polymers may photoluminesce in the solid state at room temperature when exposed to UV light. In general, the emission intensity and color may vary depending on the particular combination of metal centers and anions of the oligomeric complexes and coordination polymers. In various examples, the emission colors may be violet, blue, green or yellow. In general, the emission colors may be any color between violet and yellow. In some examples, the emission wavelength of the oligomeric complex and coordination polymer may be selected or tuned based on the metal centers, halide anions, and ligand structure of the coordination polymer.

In some examples, the oligomeric complexes and coordination polymers may emit visible light upon exposure to UV light when in the solid state at room temperature. In some examples, coordination polymer $Zn_2L^1Cl_4$ may emit yellow light. In some examples, coordination polymer $Zn_2L^1Br_4 \cdot MeOH$ may emit blue light. In some examples, coordination polymer $Zn_2L^1I_4$ may emit green light. In some examples, coordination polymer $[CdL^1Cl_2]_n \cdot nH_2O$ may emit blue light. In some examples, coordination polymer $[CdL^1Br_2] \cdot 7.5H_2O$ may emit blue light. In some examples, coordination polymer $[CdL^1I_2]_n$ may emit blue light. In some examples, coordination polymer $[HgL^1Br_2]_n$ may emit blue light. In some examples, coordination polymer $ZnL^2Cl_2$ may emit blue light. In some examples, coordination polymer $ZnL^2Br_2$ may emit blue light. In some examples, coordination polymer $[Cd(L^2)_4Cl_8]_n \cdot 2nDMF$ may emit blue light. In some examples, coordination polymer $[CdL^2Br_2]_n$ may emit blue light. In some examples, coordination polymer $[CdL^2I_2]_n$ may emit blue light.

Figure 9:
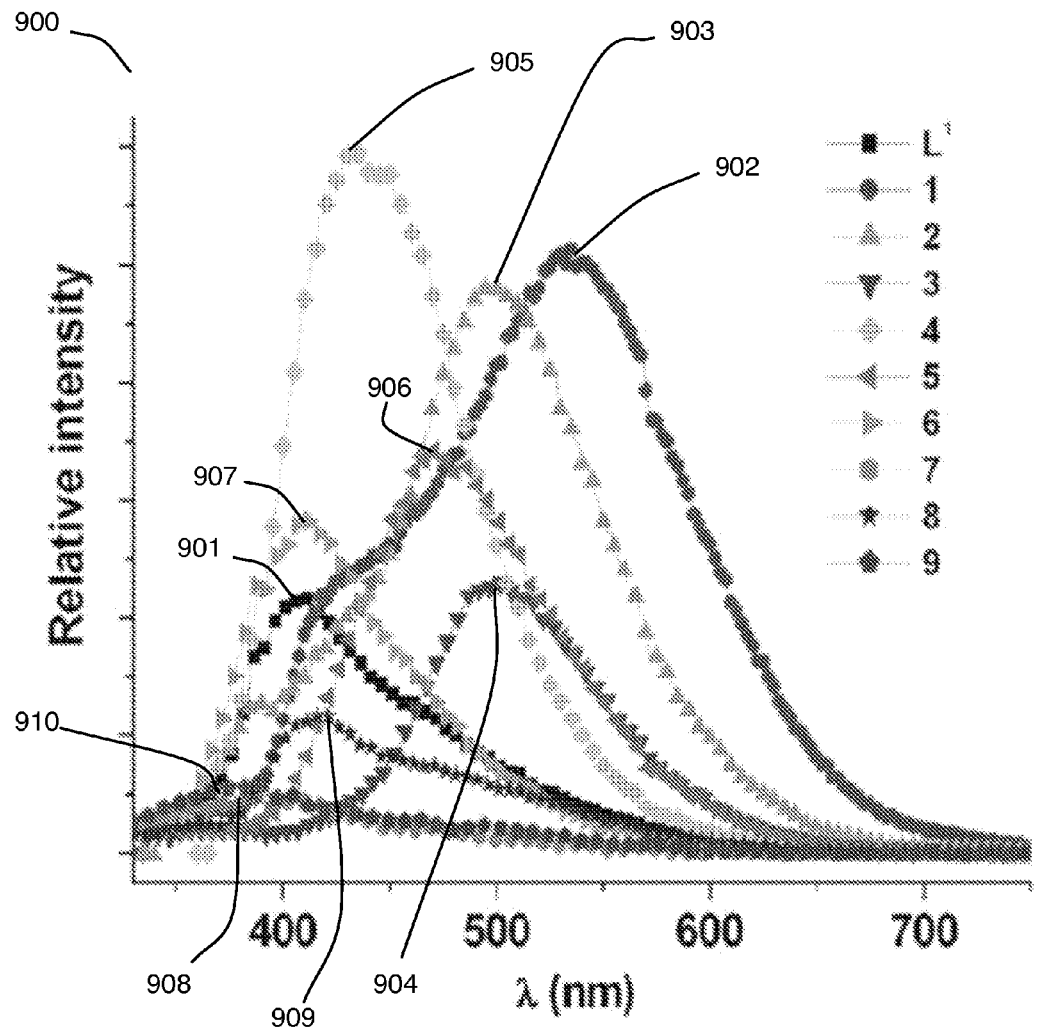
FIG. 9 is an illustration of a graph of example emission spectra for example coordination polymers.

FIG. 9 is an illustration of a graph 900 of example emission spectra for example coordination polymers in the solid state at room temperature, where the x-axis represents the emitted wavelength in nanometers, and the y-axis represents the relative intensity. The figure shows that all of the following coordination polymers emit light upon exposure to UV light when in the solid state: ligand $L^1$ (square symbols), example coordination polymer $Zn_2L^1Cl_4$ (line 1, round symbols), coordination polymer $Zn_2L^1Br_4 \cdot MeOH$ (line 2, upright triangle symbols), coordination polymer $Zn_2L^1I_4$ (line 3, upside down triangle symbols), coordination polymer $[CdL^1Cl_2]_n \cdot nH_2O$ (line 4, diamond symbols), coordination polymer $[CdL^1Br_2] \cdot 7.5H_2O$ (line 5, left facing triangle symbols), coordination polymer $[CdL^1I_2]_n$ (line 6, right facing triangle symbols), coordination polymer $[HgL^1Cl_2]_n$ (line 7, hexagon symbols), coordination polymer $[HgL^1Br_2]_n$ (line 8, star symbols), and coordination polymer $HgL^1I_2$ (line 9, pentagon symbols).

As shown, ligand $L^1$ may exhibit an emission peak 901 centered at about 411 nm upon excitation at about 315 nm. Coordination polymer $Zn_2L^1Cl_4$ may exhibit an emission peak 902 centered at about 529 nm upon excitation at about 320 nm. Coordination polymer $Zn_2L^1Br_4 \cdot MeOH$ may exhibit an emission peak 903 centered at about 493 nm upon excitation at about 310 nm. Coordination polymer $Zn_2L^1I_4$ may exhibit an emission peak 904 centered at about 494 nm upon excitation at about 320 nm. Coordination polymer $[CdL^1Cl_2]_n nH_2O$ may exhibit an emission peak 905 centered at about 435 nm upon excitation at about 310 nm. Coordination polymer $[CdL^1Br_2] \cdot 7.5H_2O$ may exhibit an emission peak 906 centered at about 471 nm upon excitation at about 310 nm. Coordination polymer $[CdL^1I_2]_n$ may exhibit an emission peak 907 centered at about 410 nm upon excitation at about 330 nm. Coordination polymer $[HgL^1Cl_2]_n$ may exhibit an emission peak 908 centered at about 388 nm upon excitation at about 310 nm. Coordination polymer $[HgL^1Br_2]_n$ may exhibit an emission peak 909 centered at about 418 nm upon excitation at about 310 nm. Coordination polymer $HgL^1I_2$ may exhibit an emission peak 910 centered at about 373 nm upon excitation at about 305 nm. FIG. 9 may show a broad and red-shifted emission bands, which may be attributed to a contribution of ligand-to-metal charge transfer (LMCT) in the example coordination polymers. The LMCT may be the result of rearrangement energy levels in the coordination polymers.

Figure 10:
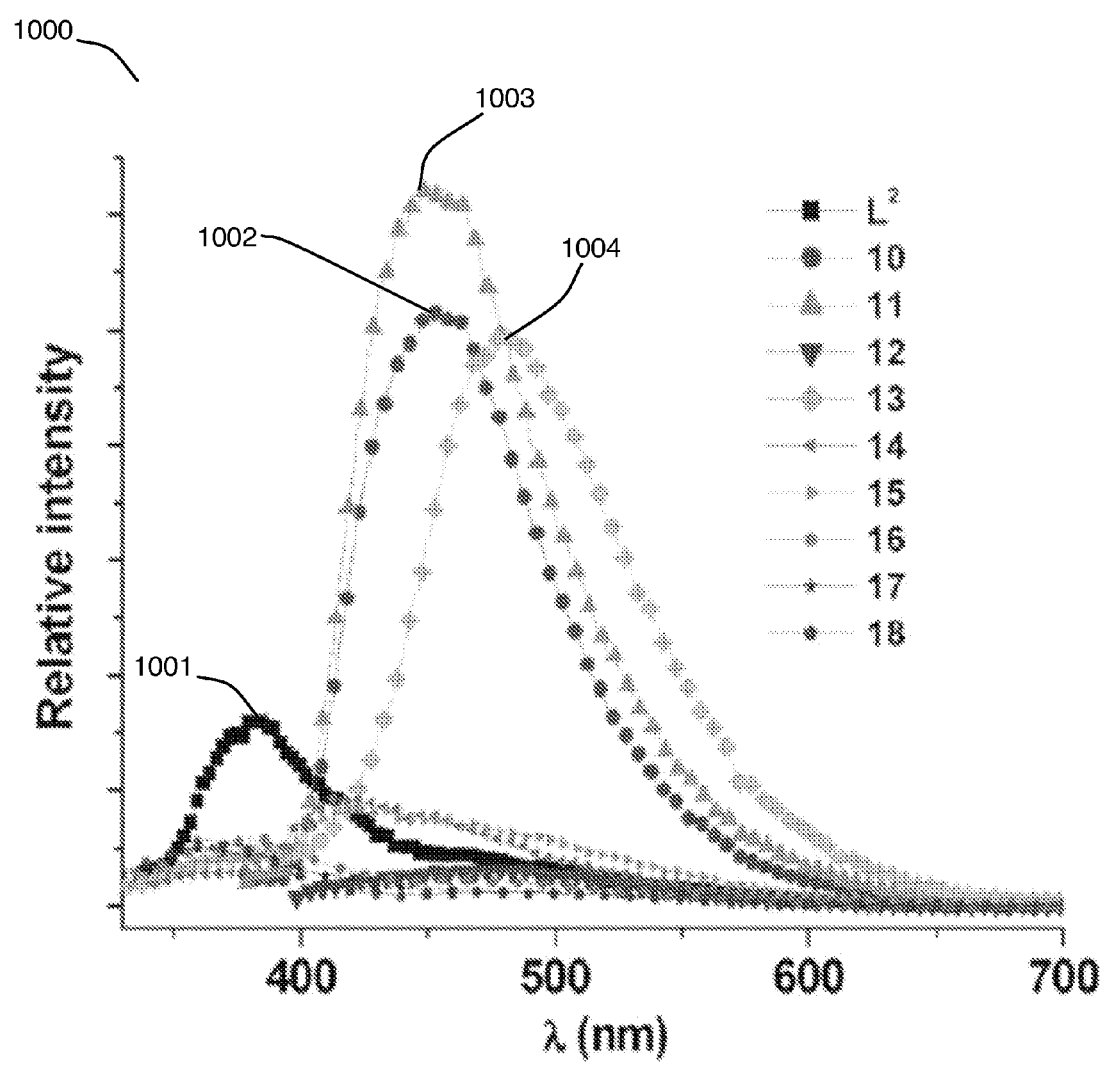
FIG. 10 is an illustration of a graph of example emission spectra for example oligomeric complexes and coordination polymers.

FIG. 10 is an illustration of a graph 1000 of example emission spectra for example oligomeric complexes and coordination polymers in the solid state at room temperature. The figure shows that all of the following oligomeric complexes and coordination polymers emit light upon exposure to UV light when in the solid state: ligand $L^2$ (square symbols), example coordination polymer $ZnL^2Cl_2$ (line 10, round symbols), coordination polymer $ZnL^2Br_2$ (line 11, triangle symbols), coordination polymer $ZnL^2I_2$ (line 12, upside down triangle symbols), coordination polymer $[Cd(L^2)_4Cl_8]_n \cdot 2nDMF$ (line 13, diamond symbols), coordination polymer $[CdL^2Br_2]_n$ (line 14, left facing triangle symbols), coordination polymer $[CdL^2I_2]_n$ (line 15, right facing triangle symbols), coordination polymer $[HgL^2Cl_2]_n \cdot 0.5nDMF$ (line 16, hexagon symbols), oligomeric complex $[Hg_2(L^2)_2Br_4] \cdot H_2O$ (line 17, star symbols), and oligomeric complex $[Hg_2(L^2)_2I_4] \cdot H_2O$ (line 18, pentagon symbols).

As shown, ligand $L^2$ may exhibit an emission peak 1001 centered at about 388 nm upon excitation at about 320 nm. Coordination polymer $ZnL^2Cl_2$ may exhibit an emission peak 1002 centered at about 456 nm upon excitation at about 360 nm. Coordination polymer $ZnL^2Br_2$ may exhibit an emission peak 1003 centered at about 448 nm upon excitation at about 360 nm. Coordination polymer $[Cd(L^2)_4Cl_8]_n \cdot 2nDMF$ may exhibit an emission peak 1004 centered at about 480 nm upon excitation at about 345 nm.

Figure 11:
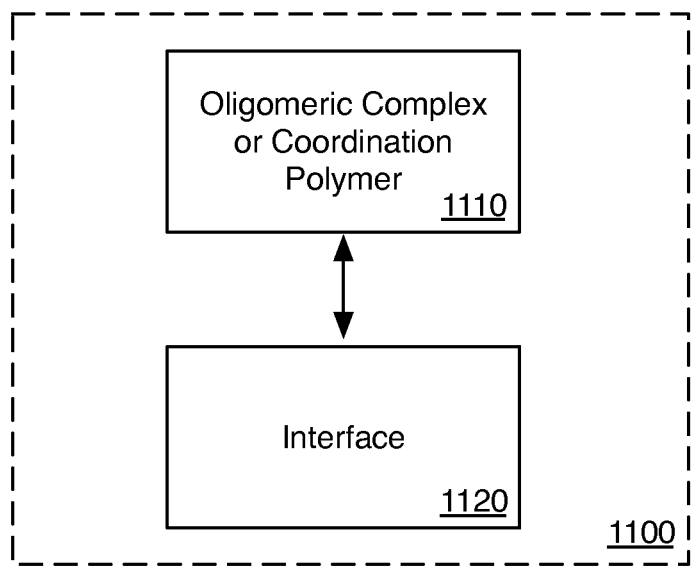
FIG. 11 is an illustration of an example device.

FIG. 11 is an illustration of an example device that may include any one or more of the coordination polymers discussed herein. As shown, device 1100 may include at least one coordination polymer 1110 and interface 1120. In general, device 1100 may be any device that may include at least one coordination polymer 1110. In some examples, device 1100 may be an optoelectronic device, an optical device, an electronic device, a magnetic device, a molecular sensing device, a catalyst, a gas adsorption unit, or the like. In some examples, device 1100 may be an optocoupler, a photocoupler, a photodiode, a phototransistor, a photomultiplier, an integrated optical circuit, a photoresistor, or the like. Oligomeric complex or coordination polymer 1100 may include any of the oligomeric complexes and coordination polymers discussed herein such as, for example, $Zn_2L^1Cl_4$, $Zn_2L^1Br_4 \cdot MeOH$, $Zn_2L^1I_4$, $[CdL^1Cl_2]_n \cdot nH_2O$, $[CdL^1Br_2] \cdot 7.5H_2O$, $[CdL^1I_2]_n$, $[HgL^1Cl_2]_n$, $[HgL^1Br_2]_n$, or $HgL^1I_2$, $ZnL^2Cl_2$, $ZnL^2Br_2$, $ZnL^2I_2$, $[Cd(L^2)_4Cl_8]_n \cdot 2nDMF$, $[CdL^2Br_2]_n$, $[CdL^2I_2]_n$, $[HgL^2Cl_2]_n \cdot 0.5nDMF$, $[Hg_2(L^2)_2Br_4] \cdot H_2O$, or $[Hg_2(L^2)_2I_4] \cdot H_2O$, or the like.

In general, interface 1120 may include any suitable structures, materials or devices for components in device 1100 or outside devices that may interface with device 1100 to interface with oligomeric complex or coordination polymer 1110. In various examples, the interface may be an electrical interface, an optical interface, a physical interface, or the like. In some examples, interface 1120 may include an electrode or electrodes. In some examples, interface 1120 may include an optical light guide or guides. In some examples, interface 1120 may include wires, pins, ball grid arrays, or the like.

EXAMPLES

Example 1

Physical Measurements $^1$H NMR spectra were recorded on a Bruker AVANCE spectrometer (400 MHz). FT-IR spectra were recorded in the

Example 2

Preparation of Monomer Compound L¹

4,4'-Dipyridylamine (4.28 g, 25 mmol), 1,4-dibromobenzene (2.36 g, 10 mmol), anhydrous potassium carbonate (4.8 g, 34.4 mmol), cupric sulfate (994 mg, 6.2 mmol), 18-crown-6 (220 mg, 0.83 mmol), and diphenyl ether (35 mL) were added to a three-necked flask and heated at 200 degrees C. under nitrogen for 3 days, then additional 1,4-dibromobenzene (7 g, 29.7 mmol) was added. The reaction mixture was stirred at 200 degrees C. for another day. After the reaction was cooled, dichloromethane and water were added to dissolve the solid, and the organic phase was washed with distilled water to neutral pH and then dried with sodium sulfate. After removal of the solvent, the residue was purified by a silica gel chromatography to afford colorless solids of the following two compounds: (4-bromophenyl)-di(4-pyridyl) amine (2.92 g, yield 36% based on 4,4'-dipyridylamine). $^1$H NMR (CDCl$_3$, 400 MHz): δ=8.45 (d, J=8.0 Hz, 4H, pyridyl-H), 7.56 (d, J=11 Hz, 2H, phenylene-H), 7.08 (d, J=11 Hz, 2H, phenylene-H), 6.96 (d, J=8.0 Hz, 4H, pyridyl-H); N,N,N',N'-tetra(4-pyridyl)-1,4-phenylenediamine (L¹; 2.1 g, 40.8% based on 4,40-dipyridylamine). $^1$H NMR (CDCl$_3$, 500 MHz): δ=8.49 (d, J=6.0 Hz, 8H, pyridyl-H), 7.23 (s, 4H, phenylene-H), 7.01 (d, J=6.0 Hz, 8H, pyridyl-H). Anal. Calcd (%) for C$_{26}$H$_{20}$N$_6$: C, 74.98; H, 4.84; N, 20.18. Found: C, 74.57; H, 4.71; N, 20.06. IR (KBr pellet, cm$^{-1}$): 1592(s), 1577 (vs), 1498(s), 1488(s), 130(m), 1304(s), 1277(vs), 1217(m), 993(m), 813(m), 740(w), 624(m), 542(m).

Example 3

Preparation of Monomer Compound L²

A mixture of 2,2'-dipyridylamine (5.27 g, 30.76 mmol), (4-bromophenyl)-di(4-pyridyl)amine (2.50 g, 7.69 mmol), anhydrous potassium carbonate (2.66 g, 19.23 mmol), bronze powder (4.93 g, 77.64 mmol), 18-crown-6 (200 mg, 0.76 mmol), and DMF (125 mL) was heated at 145 degrees C. under nitrogen for 30 hours. The reaction was cooled and worked up by a procedure similar to that for L¹. A yellowish solid was collected from a silica gel column, and was further purified by recrystallization from dichloromethane and petroleum ether, to afford a white solid of N,N-di(2-pyridyl)-N', N'-di(4-pyridyl)-1,4-phenylenediamine (L², 1.32 g, yield: 41%). $^1$H NMR (CDCl$_3$, Bruker 400 MHz): 8.43 (d, J=4.4 Hz, 4H, pyridyl-H), 8.37 (d, J=3.6 Hz, 2H, pyridyl-H), 7.60-7.65 (m, 2H, pyridyl-H), 7.21 (d, J=8.8 Hz, 2H, phenylene-H), 7.14 (d, J=8.8 Hz, 2H, phenylene-H), 6.98-7.09 (m, 8H, pyridyl-H). Anal. Calcd (%) for C$_{26}$H$_{20}$N$_6$: C, 74.98; H, 4.84; N, 20.18. Found: C, 74.53; H, 4.72; N, 19.89. IR (KBr pellet, cm$^{-1}$): 1575(vs), 1505(s), 1490(s), 1467(s), 1431(vs), 1324(s), 1305.13 (s), 1276(s), 1218(m), 1163(w), 1103(w), 991(m), 811(m), 777(m), 737(w), 654(w), 622(m), 530(m).

Example 4

Preparation of Complex Zn$_2$L¹Cl$_4$ (1)

A mixture of L¹ (20.8 mg, 0.05 mmol) and ZnCl$_2$ (14 mg, 0.1 mmol) in MeOH (50 mL) was refluxed for 3 hours. After cooling to room temperature, the yellowish microcrystalline precipitate was collected, washed with methanol, and dried. Yield: 14 mg, 42%. Anal. (%) calcd. for C$_{26}$H$_{20}$Cl$_4$N$_6$Zn$_2$: C, 45.32; H, 2.93; N, 12.20. Found: C, 45.39; H, 3.06; N, 12.09. IR (KBr pellet, cm$^{-1}$): 3424(br), 2921(w), 1613(s), 1583(s), 1498(s), 1367(w), 1351(m), 1258(w), 1221(m), 1066(s), 1021(vs), 819(w), 646(w), 545(m), 466(m)

Example 5

Preparation of Complex Zn$_2$L¹Br$_4$3MeOH (2)

Compound 2 was prepared by a procedure similar to that for 1, using ZnBr$_2$ (23 mg, 0.1 mmol) in place of ZnCl$_2$. A yellowish microcrystalline product was obtained. Yield: 22 mg, 49%. Anal. (%) Calcd. for C$_{27}$H$_{24}$Br$_4$N$_6$OZn$_2$: C, 36.08; H, 2.69; N, 9.35. Found: C, 35.86; H, 2.77; N, 9.05. IR (KBr pellet, cm$^{-1}$): 3423(br), 3047(w), 1616(s), 1582(vs), 1545 (w), 1498(vs), 1448(w), 1346(m), 1317(m), 1216(w), 1068 (m), 1020(m), 825(m), 635(m), 547(m), 472(w).

Example 6

Preparation of Complex Zn$_2$L¹I$_4$ (3)

Compound 3 was prepared by a procedure similar to that for 1, using ZnI$_2$ (32 mg, 0.1 mmol) in place of ZnCl$_2$. Yellowish microcrystalline solid was obtained. Yield: 25 mg, 34%. Anal. (%) calcd. for C$_{26}$H$_{20}$I$_4$N$_6$Zn$_2$: C, 29.60; H, 1.91; N, 7.97. Found: C, 29.54; H, 2.16; N, 7.86. IR (KBr pellet, cm$^{-1}$): 3445(br), 1616(s), 1597(vs), 1560(w), 1545(w), 1497 (vs), 1439(w), 1349(m), 1337(m), 1311(m), 1284(m), 1213(s), 1061(m), 1025(s), 823(m), 734(w), 646(m), 539(m), 458(w).

Example 7

Preparation of Coordination Polymer [CdL¹Cl$_2$]$_n$.nH$_2$O (4)

A mixture of L¹ (4.2 mg, 0.01 mmol), Cd(NO$_3$)$_2$.4H$_2$O (6.2 mg, 0.02 mmol), and NaCl (2.4 mg, 0.04 mmol) in DMSO, DMF, H$_2$O, and MeOH (8: 8:16:1) was sealed in a small vial, which was heated to 120 degrees C. for 90 hours. After cooling to room temperature, colorless block crystals of 4 suitable for X-ray structure determination were obtained. Yield: 4 mg, 65%. Anal. (%) calcd. for C$_{26}$H$_{22}$CdCl$_2$N$_6$O: C, 50.55; H, 3.59; N, 13.60%. Found: C, 50.49; H, 4.03; N, 13.59. IR (KBr pellet, cm$^{-1}$): 3427(br, H2O), 3048(w), 2970 (w), 2924(w), 2355(w), 1673(m), 1605(m), 1586(s), 1562 (w), 1548(w), 1493(s), 1338(w), 1308(m), 1280(m), 1215 (m), 1089(w), 1049(w), 1006(m), 935(w), 824(w), 793(w), 702(w), 634(m), 546(m).

Example 8

Preparation of Complex [CdL¹Br$_2$].7.5H$_2$O (5)

Compound 5 was prepared by a procedure similar to that for 1, using KBr (24 mg, 0.2 mmol) and Cd(NO$_3$)2.4H$_2$O (31 mg, 0.1 mmol) in place of ZnCl$_2$. A yellowish microcrystalline product was obtained. Yield: 25 mg, 64%. Anal. (%) calcd. for C$_{26}$H$_{35}$Br$_2$CdN$_6$O$_{7.5}$: C, 37.91; H, 4.28; N, 10.20%. Found: C, 38.13; H, 4.63; N, 9.74. IR (KBr pellet, cm$^{-1}$): 3426(m, br), 3038(w), 2922(w), 1607(s), 1583(vs), 1494(vs), 1434(w), 1384(vs), 1342(s), 1312(s), 1279(m), 1218(s), 1013(s), 944(w), 819(m), 735(w), 703(w), 635(m), 541(m), 473(w).

Example 9

Preparation of Coordination Polymer $[CdL^1I_2]_n$ (6)

Compound 6 was prepared by a procedure similar to that for 4, using KI (6.6 mg, 0.04 mmol) in place of NaCl. Colorless block crystals of 6 suitable for X-ray structure determination were obtained. Yield: 4 mg, 54%. Anal. (%) calcd. for $C_{26}H_{20}CdI_2N_6$: C, 39.90; H, 2.58; N, 10.74. Found: C, 40.16; H, 2.72; N, 10.67. IR (KBr pellet, $cm^{-1}$): 3423(m, br), 3050 (w), 2969.49 (w), 1610(vs), 1581(vs), 1564(s), 1544(m), 1496(vs), 1444(m), 1411(w), 1345(vs), 1274(w), 1255(w), 1226(s), 1104(w), 1067(m), 1013(s), 993(w), 943(w), 835 (m), 823(vs), 740(w), 704(w), 634(vs), 544(s), 438(w).

Example 10

Preparation of Coordination Polymer $[HgL^1Cl_2]_n$ (7)

A mixture of $L^1$ (4.16 mg, 0.01 mmol) and $HgCl_2$ (5.4 mg, 0.02 mmol) in DMSO, DMF, and H2O (70:70:10) was refluxed for 3 hours in air, then transferred in a small vial Teflon stainless container, which was heated to 120 degrees C. for 90 hours. After cooling to room temperature, colorless block crystals of 7 suitable for X-ray structure determination were obtained. Yield: 5 mg, 72%. Anal. (%) calcd. for $C_{26}H_{20}Cl_2HgN_6$: C, 45.39; H, 2.93; N, 12.22. Found: C, 45.42; H, 3.28; N, 12.31. IR (KBr pellet, $cm^{-1}$): 3440(br), 1605(s), 1580(vs), 1546(w), 1493(s), 1439(w), 1343(s), 1316 (m), 1275(w), 1217(m), 1065(w), 1006(m), 834(w), 823(m), 702(w), 631(m), 542(m).

Example 11

Preparation of Coordination Polymer $[HgL^1Br_2]_n$ (8)

Compound 8 was prepared by a procedure similar to that for 4, using KBr (6.6 mg, 0.04 mmol) and $Hg(NO_3)_2 \cdot \frac{1}{2}H_2O$ (6.7 mg, 0.02 mmol) in place of NaCl and $Cd(NO_3)_2 \cdot 4H_2O$, respectively. Colorless block crystals of 8 suitable for X-ray structure determination were obtained. Yield: 4 mg, 52%. Anal. (%) calcd. for $C_{26}H_{20}Br_2HgN_6$: C, 40.20; H, 2.59; N, 10.82. Found: C, 40.12; H, 2.71; N, 10.81. IR (KBr pellet, $cm^{-1}$): 3417(s), 1607(m), 1580(vs), 1505(m), 1492(m), 1439 (w), 1399(m), 1384(m), 1343(m), 1316(w), 1225(w), 1145 (w), 1066(w), 1005(s), 993(s), 834(w), 822(m), 702(w), 631 (m), 543(m).

Example 12

Preparation of Complex $HgL^1I_2$ (9)

Compound 9 was prepared by a procedure similar to that for 1, using $HgI_2$ (45.5 mg, 0.1 mmol) in place of $ZnCl_2$. Yellowish microcrystalline solid was obtained. Yield: 26 mg, 60%. Anal. (%) calcd. for $C_{26}H_{20}I_2HgN_6$: C, 35.86; H, 2.31; N, 9.65. Found: C, 35.76; H, 2.34; N, 9.57. IR (KBr pellet, $cm^{-1}$): 3441(br), 3052(w), 1605(s), 1580.08 (vs), 1545(m), 1492(vs), 1439(w), 1341(s), 1315(s), 1282(w), 1223(m), 1105(w), 1006(s), 834(m), 821(m), 739(w), 702(w), 632(m), 542(m).

Example 13

Preparation of Complex $ZnL^2Cl_2$ (10)

A mixture of $L^2$ (20.8 mg, 0.05 mmol), $ZnCl_2$ (14 mg, 0.1 mmol) in MeOH (50 mL) was refluxed for 3 hours in air. After slow cooling to the room temperature, a yellowish microcrystalline solid was obtained. Yield: 15 mg, 54%. Anal. (%) calcd. for $C_{26}H_{20}Cl_2N_6Zn$: C, 56.49; H, 3.65; N, 15.20. Found: C, 56.27; H, 3.75; N, 15.10. IR (KBr pellet, $cm^{-1}$): 3440(br), 1598(vs), 1497(s), 1466(m), 1430(s), 1341(m), 1217(m), 1064(w), 1024(m), 825(w), 772(w), 740(w), 655 (w), 537(w).

Example 14

Preparation of Complex $ZnL^2Br_2$ (11)

Compound 11 was prepared by a procedure similar to that for 10, using $ZnBr_2$ (23 mg, 0.1 mmol) in place of $ZnCl_2$. A yellowish microcrystalline solid was obtained. Yield: 16 mg, 50%. Anal. (%) calcd. for $C_{26}H_{20}Br_2N_6Zn$: C, 48.67; H, 3.14; N, 13.10. Found: C, 48.44; H, 3.57; N, 13.06. IR (KBr pellet, $cm^{-1}$): 3441(br), 1622(m), 1599(vs), 1496(s), 1464(m), 1430(s), 1340(m), 1216(m), 1065(w), 1025(m), 825(w), 775 (w), 739(w), 654(w), 538(w), 469(w).

Example 15

Preparation of Complex $ZnL^2I_2$ (12)

Compound 12 was prepared by a procedure similar to that for 10, using $ZnI_2$ (32 mg, 0.1 mmol) in place of $ZnCl_2$. Yellowish microcrystalline solid was obtained. Yield: 21 mg, 56%. Anal. (%) calcd. for $C_{26}H_{20}I_2ZnN_6$: C, 42.45; H, 2.74; N, 11.42. Found: C, 42.16; H, 3.19; N, 11.37. IR (KBr pellet, $cm^{-1}$): 3445(br), 1616(m), 1597(vs), 1497(s), 1439(s), 1337 (m), 1311(m), 1284(m), 1213(s), 1061(m), 1025(s), 823(m), 734(w), 646(w), 539(w), 458(w).

Example 16

Preparation of Coordination Polymer $[Cd_4(L2)_4Cl_8]_n \cdot 2nDMF$ (13)

Compound 13 was prepared by a procedure similar to that for 4, using $L^2$ (4.16 mg, 0.01 mmol) in place of $L^1$. Colorless block crystals of 13 suitable for X-ray structure determination were obtained. Yield: 3 mg, 70%. Anal. Calcd for $C_{110}H_{94}Cd_4Cl_8N_{26}O_2$: C, 51.91; H, 3.72; N, 14.31. Found: C, 51.69; H, 4.11; N, 14.31. IR (KBr pellet, $cm^{-1}$): 3421(br), 3060(w), 2922(w), 1670(m), 1591(vs), 1564(m), 1545(s), 1468(s), 1429(vs), 1386(w), 1326(m), 1272(m), 1221(s), 1151(w), 1095(w), 1064(w), 1015(m), 820(m), 778(m), 738 (m), 657(w), 628(m), 535(m), 458(w).

Example 17

Preparation of Coordination Polymer $[CdL^2Br_2]_n$ (14)

A mixture of $L^2$ (4.16 mg, 0.01 mmol), $Cd(NO_3)_2 \cdot 4H_2O$ (6.6 mg, 0.02 mmol), and KBr (4.8 mg, 0.04 mmol) in DMSO, DMF, and $H_2O$ (100:100:10) was sealed in a small vial, which was heated to 120 degrees C. for 90 hours. After cooling to room temperature, colorless block crystals of 14 suitable for X-ray structure determination were obtained.

Yield: 4 mg, 55%. Anal. (%) calcd. for $C_{26}H_{20}Br_2CdN_6$: C, 45.34; H, 2.93; N, 12.20. Found: C, 44.93; H, 2.92; N, 12.16. IR (KBr pellet, cm$^{-1}$): 3441(br), 3064(w), 1614(s), 1581(vs), 1541(w), 1504(vs), 1482(vs), 1458(s), 1434(vs), 1347(s), 1313(vs), 1269(s), 1252(m), 1216(s), 1154(m), 1112(w), 1061(m), 1016(vs), 992(w), 935(w), 835(w), 818(s), 781(m), 741(m), 708(w), 657(w), 643(m), 634(m), 622(m), 532(m), 465(m).

Example 18

Preparation of Coordination Polymer $[CdL^2I_2]_n$ (15)

Compound 15 was prepared by a procedure similar to that for 14, using KI (6.6 mg, 0.04 mmol) in place of KBr. Colorless block crystals of 15 suitable for X-ray structure determination were obtained. Yield: 4 mg, 51%. Anal. (%) calcd. for $C_{26}H_{20}I_2CdN_6$: C, 39.90; H, 2.58; N, 10.74. Found: C, 39.99; H, 2.59; N, 10.70. IR (KBr pellet, cm$^{-1}$): 3441(br), 3061(w), 1615(s), 1603(s), 1581(vs), 1541(w), 1500(vs), 1483(vs), 1460(s), 1434(vs), 1349(s), 1314(vs), 1269(s), 1252(m), 1216(s), 1156(m), 1062(m), 1018(vs), 992(w), 839(w), 818(s), 783(m), 741(m), 708(w), 656(w), 644(m), 635(m), 622(m), 533(m), 466(m).

Example 19

Preparation of Coordination Polymer $[HgL^2Cl_2]_n \cdot 0.5nDMF$ (16)

Compound 16 was prepared by a procedure similar to that for 7, using $L^2$ (4.16 mg, 0.01 mmol) in place of $L^1$. Colorless block crystals of 16 suitable for X-ray structure determination were obtained. Yield: 5 mg, 71%. Anal. (%) calcd. for $C_{55}H_{47}Cl_4Hg_2N_{13}O$: C, 45.59; H, 3.27; N, 12.57. Found: C, 45.39; H, 3.49; N, 12.27. IR (KBr pellet, cm$^{-1}$): 3445(br), 2920(w), 1591(s), 1577(vs), 1549(m), 1498(s), 1417(w), 1342(m), 1304(s), 1277(s), 1217(m), 993(m), 935(w), 848(w), 813(m), 740(w), 693(w), 624(m), 542(m), 528(w).

Example 20

Preparation of Oligomeric Complex $[Hg_2(L^2)_2Br_4]\cdot 3H_2O$ (17)

Compound 17 was prepared by a procedure similar to that for 14, using $Hg(NO_3)_2 \cdot 0.5H_2O$ (6.7 mg, 0.02 mmol) in place of $Cd(NO_3)_2 \cdot 4H_2O$. Colorless block crystals of 17 suitable for X-ray structure determinations were obtained. Yield: Anal. (%) calcd. for $C_{52}H_{42}Br_4Hg_2N_{12}O$: C, 39.74; H, 2.69; N, 10.69. Found: C, 39.49; H, 2.89; N, 10.48. IR (KBr pellet, cm$^{-1}$): 3424(br), 3047(w), 1586(vs), 1543(w), 1504(s), 1467(s), 1428(s), 1324(m), 1312(m), 1265(m), 1212(m), 1151(w), 1055(w), 1010(m), 826(w), 775(m), 737(m), 709(w), 642(m), 625(w), 536(m).

Example 21

Preparation of Oligomeric Complex $[Hg_2(L^2)_2I_4]\cdot 3H_2O$ (18)

Compound 18 was prepared by a procedure similar to that for 14, using $HgI_2$ (9.1 mg, 0.02 mmol) in place of $Cd(NO_3)_2 \cdot 4H_2O$ and KBr. Colorless block crystals of 18 suitable for X-ray structure determination were obtained. Yield: 4 mg, 47%. Anal. (%) calcd. for $C_{52}H_{42}Hg_2I_4N_{12}O$: C, 35.49; H, 2.41; N, 9.55. Found: C, 35.13; H, 2.50; N, 9.39. IR (KBr pellet, cm$^{-1}$): 3424(br), 3045(w), 2921(w), 2361(w), 1586(vs), 1543(w), 1505(s), 1467(s), 1428(s), 1325(m), 1312(m), 1266(m), 1212(m), 1149(w), 1058(w), 1007(m), 825(w), 774(m), (m), 709(w), 642(m), 624(w), 535(m), 472(w).

Example 22

Photoluminescence

Ligands L1, L2, and complexes 1-18 exhibit photoluminescence in the solid state at room temperature when exposed to UV light. The emission intensity and color strongly depend on the metal centers and the anions. The colors vary from violet (for 8 and 16) to yellow (for 1).

To more clearly understand the luminescent properties, the emission spectra of the compounds were measured in the solid state. The ligand L1 exhibits a medium-intensity emission centered at 411 nm (FIG. 9) upon excitation at 315 nm. For complexes 1, 2, 4, and 5, intense emission bands are observed at 529, 493, 435, and 471 nm, respectively, upon excitation at 320, 325, 310, and 310 nm, respectively. While not intending to be bound by theory, the origin of the broad and red-shifted emission bands may be tentatively attributed to the contribution of ligand-to-metal charge transfer (LMCT), which results in the rearrangement of energy levels. The differences in the band positions might also be related to the differences in the metal centers and the local coordination environments. The significantly stronger fluorescence of these complexes compared with ligand L1 may be ascribed to the coordination effect, which effectively reduces the loss of energy through a nonradiative pathway by suppression of the rotation of the pyridyl rings and increasing the rigidity of the ligand.

Complexes 7, 8, and 9 exhibit emission bands entered at 388, 414, and 373 nm, respectively, upon excitation at 310, 310, and 305 nm, respectively. The emission of these Hg(II) complexes are significantly weaker than that of $L^1$, which may be ascribed to the heavy-atom effect. In contrast, medium-intensity emission bands are observed at 494 and 410 nm for complexes 3 and 6, respectively, upon excitation at 320, and 330 nm, respectively. The emission intensities are similar to that of $L^1$, which may be attributed to the balance of fluorescence increasing and decreasing effects caused by the coordination effect and the heavy atom effect, respectively.

Similar to $L^1$, the ligand $L^2$ exhibits a medium-intensity emission centered at 388 nm (FIG. 10) upon excitation at 320 nm. Complexes 10, 11, and 13 exhibit intense emission bands at 456, 448, and 480 nm, respectively, upon excitation at 360, 360, and 345 nm, respectively. All other complexes of $L^2$ exhibit rather weak emission at shorter wavelengths. The variation in emission intensities can also be rationalized in terms of the coordination effect and the heavy atom effect.

Ligands $L^1$, $L^2$, and complexes 1-18 exhibited solid state emissions, with the colors varying from violet to yellow, and the maxima wavelengths varying in a large range of 373-529 nm. In addition, the emission intensities also vary to a large extent. These complexes are good examples of photoluminescent compounds with emission wavelengths and intensities modulated by the change of the ligands, the central atoms, and the anions.

Example 23

Systems

Figure 12:
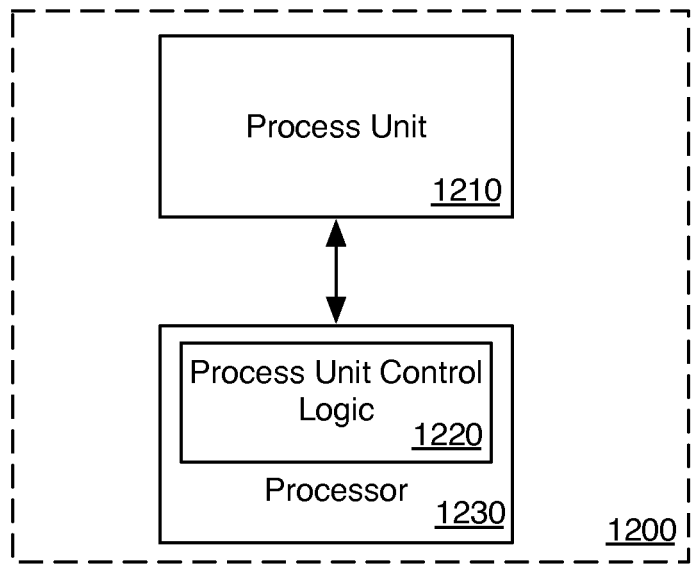
FIG. 12 is an illustration of an example system for producing ligands, oligomeric complexes or coordination polymers.

Turning now to other embodiments that may perform any of the methods as described herein, FIG. 12 illustrates an example system 1200 for producing the ligands, oligomeric complexes, and/or coordination polymers discussed herein in accordance with at least some embodiments of the present disclosure. System 1200 may be used to perform some or all of the functions described. System 1200 may include a process unit 1210 operably coupled to a processor 1230 that may include process unit control logic 1220. Process unit 1210 may include any or all of the process unit characteristics as described herein. In some examples, process unit 1210 may include a reaction vessel, various ports, various pressure ports, a process jacket, one or more agitators, a cover, or the like. In some examples, process unit 1210 may include electro-mechanical devices that may be utilized to actuate the various components. In some examples, the ports may include or be in-line with valves that may be operable under applied signals, such as, for example, communication signals. In some examples, the ports may be connected to additional vessels that may provide the reaction materials. In some examples, the ports may be attached to vessels that may collect materials, such as, for example, processed ligands, oligomeric complexes, and/or coordination polymers. In some examples, the cover may be operable by a motor or other device such that it may be removed under the operation of applied signals, such as, for example, communication signals. In some examples, a liquid flow through a process jacket may be controlled under the operation of applied signals, such as, for example, communication signals. In some examples, the components of the process unit may be housed in a chamber. The process unit may also include electro-mechanical devices that may be configured to actuate the various components. In some examples, some of the components may be automatically or robotically actuated.

In some examples, system 1200 may include a processor 1230. In some examples, processor 1230 may be implemented as part of a computer system. System 1200 may include process unit control logic 1220 that may be configured to undertake various methods, functional operations, actions, or blocks such as those described previously. Further, system 1200 may include additional items such as memory, a router, network interface logic, etc. Process unit control logic 1220 may be configured to provide any of the functionality described herein and claimed subject matter is not limited to specific types or manifestations of processing logic. For example, processor 1230 may be a microprocessor or Central Processing Unit (CPU). In other implementations, processor 1230 may be an Application Specific Integrated Circuit (ASIC), a Field Programmable Gate Array (FPGA), a digital signal processor (DSP), or other integrated formats. Processor 1230 and process unit 1210 may communicate by various suitable means, such as, for example, by wired connections or wireless connections.

FIG. 13 illustrates an example computer program product 1300 arranged in accordance with at least some embodiments of the present disclosure. Computer program product 1300 may include a signal bearing medium 1302. Signal bearing medium 1302 may include one or more machine-readable instructions 1304, which, when executed by one or more processors, may operatively enable a computing device to provide the functionality described herein. Thus, for example, referring to the system of FIG. 12, processor 1230 may undertake one or more of the actions discussed herein in response to instructions 1304 conveyed by medium 1302.

In some implementations, signal bearing medium 1302 may encompass a computer-readable medium 1306, such as, but not limited to, a hard disk drive, a Compact Disc (CD), a Digital Video Disk (DVD), a digital tape, memory, etc. In some implementations, signal bearing medium 1302 may encompass a recordable medium 1308, such as, but not limited to, memory, read/write (R/W) CDs, R/w DVDs, etc. In some implementations, signal bearing medium 1302 may encompass a communications medium 1310, such as, but not limited to, a digital and/or an analog communication medium (e.g., a fiber optic cable, a waveguide, a wired communication link, a wireless communication link, etc.).

Figure 14:
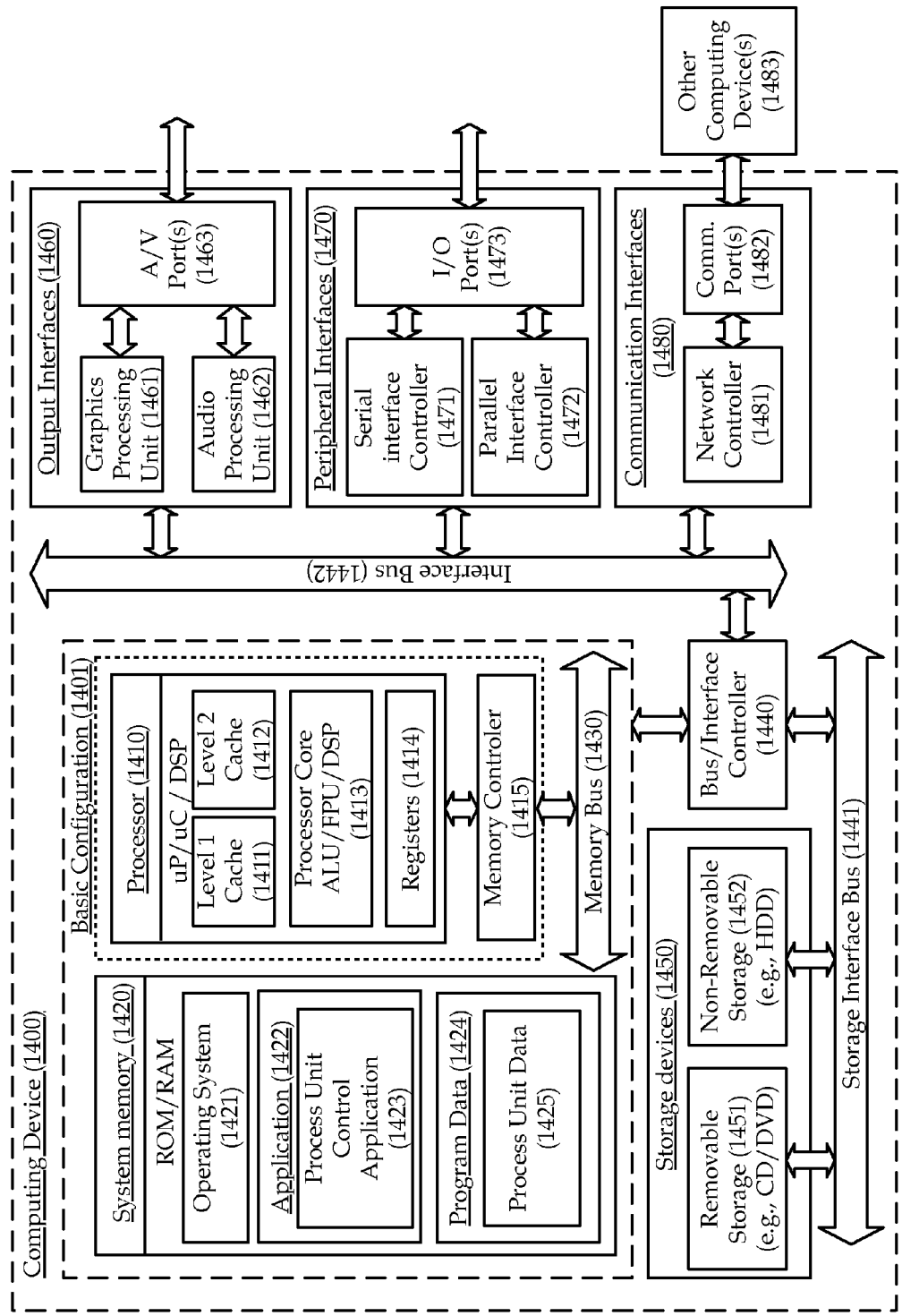
FIG. 14 is a block diagram illustrating an example computing device.

FIG. 14 is a block diagram illustrating an example computing device 1400 that is arranged in accordance with at least some embodiments of the present disclosure. In some examples, basic configuration 1401, computing device 1400 may include one or more processors 1410 and system memory 1420. A memory bus 1430 can be used for communicating between the processor 1410 and the system memory 1420.

Depending at least in part on the configuration, processor 1410 may be of a wide variety of types including but not limited to a microprocessor ($\mu P$), a microcontroller ($\mu C$), a digital signal processor (DSP), or any combination thereof. Processor 1410 can include one or more levels of caching, such as a level one cache 1411 and a level two cache 1412, a processor core 1413, and registers 1414. The processor core 1413 can include an arithmetic logic unit (ALU), a floating point unit (FPU), a digital signal processing core (DSP Core), or any combination thereof. A memory controller 1415 can also be used with the processor 1410, or in some implementations the memory controller 1415 can be an internal part of the processor 1410.

Depending at least in part on the configuration, the system memory 1420 may be of any type including but not limited to volatile memory (such as RAM), non-volatile memory (such as ROM, flash memory, etc.) or any combination thereof. System memory 1420 may include an operating system 1421, one or more applications 1422, and program data 1424. Application 1422 may include process unit control application 1423 that can be arranged to perform the functions, actions, and/or operations as described herein including the functional blocks, actions, and/or operations described with respect to FIGS. 1 to 4. Program Data 1424 may include process unit data 1425 for use with the flash memory algorithm 1423. In some example embodiments, application 1422 may be arranged to operate with program data 1424 on an operating system 1421. This described basic configuration is illustrated in FIG. 14 by those components within dashed line 1401.

Computing device 1400 may have additional features or functionality, and additional interfaces to facilitate communications between the basic configuration 1401 and any required devices and interfaces. For example, a bus/interface controller 1440 may be used to facilitate communications between the basic configuration 1401 and one or more data storage devices 1450 via a storage interface bus 1441. The data storage devices 1450 may be removable storage devices 1451, non-removable storage devices 1452, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid-state drives (SSD), and tape drives to name a few. Example computer storage media may include volatile and nonvolatile, removable and non-removable media implemented in any method or technology for storage of information, such as computer readable instructions, data structures, program modules, or other data.

System memory 1420, removable storage 1451 and non-removable storage 1452 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the information and which may be accessed by computing device 1400. Any such computer storage media may be part of device 1400.

Computing device 1400 may also include an interface bus 1442 for facilitating communication from various interface devices (e.g., output interfaces, peripheral interfaces, and communication interfaces) to the basic configuration 1401 via the bus/interface controller 1440. Example output interfaces 1460 may include a graphics processing unit 1461 and an audio processing unit 1462, which may be configured to communicate to various external devices such as a display or speakers via one or more A/V ports 1463. Example peripheral interfaces 1470 may include a serial interface controller 1471 or a parallel interface controller 1472, which may be configured to communicate with external devices such as input devices (e.g., keyboard, mouse, pen, voice input device, touch input device, etc.) or other peripheral devices (e.g., printer, scanner, etc.) via one or more I/O ports 1473. An example communication interface 1480 includes a network controller 1481, which may be arranged to facilitate communications with one or more other computing devices 1483 over a network communication via one or more communication ports 1482. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 1400 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 1400 may also be implemented as a personal computer including both laptop computer and non-laptop computer configurations. In addition, computing device 1400 may be implemented as part of a wireless base station or other wireless system or device.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, is considered to be a self-consistent sequence of operations or similar processing leading to a result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing device, that manipulates or transforms data represented as physical electronic or magnetic quantities within memories, registers, or other information storage devices, transmission devices, or display devices of the computing device.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Video Disk (DVD), a digital tape, a computer memory, etc.; and a transmission type medium such as a digital and/or an analog communication medium (e.g., a fiber optic cable, a waveguide, a wired communication link, a wireless communication link, etc.).

The herein described subject matter sometimes illustrates different components contained within, or connected with, different other components. It is to be understood that such depicted architectures are merely examples and that in fact many other architectures can be implemented which achieve the same functionality. In a conceptual sense, any arrangement of components to achieve the same functionality is effectively "associated" such that the functionality is achieved. Hence, any two components herein combined to achieve a particular functionality can be seen as "associated with" each other such that the functionality is achieved, irrespective of architectures or intermedial components. Likewise, any two components so associated can also be viewed as being "operably connected", or "operably coupled", to each other to achieve the functionality, and any two components capable of being so associated can also be viewed as being "operably couplable", to each other to achieve the functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While certain example techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

What is claimed:

1. An oligomeric complex or a coordination polymer comprising:
   at least two ligands, wherein at least one of the at least two ligands comprises N,N,N',N'-tetra(4-pyridyl)-1,4-phenylenediamine; and
   at least two metal atoms structurally incorporated with the ligands.

2. The oligomeric complex or coordination polymer of claim 1, wherein at least one other of the two ligands comprises:
   a central linker portion comprising at least one of a phenylenediamine group, a phenyl group, a terphenyl group, a biphenyl group, poly-aromatic hydrocarbon (PAH) group, or a (methylbenzene)$_2$ group; and
   four pyridyl groups defined as pyridyl group $Py^1$, pyridyl group $Py^2$, pyridyl group $Py^3$, and pyridyl group $Py^4$, wherein pyridyl group $Py^1$ is covalently bonded to the central linker portion, pyridyl group $Py^2$ is covalently bonded to the central linker portion, pyridyl group $Py^3$ is covalently bonded to the central linker portion, and pyridyl group $Py^4$ is covalently bonded to the central linker portion.

3. The oligomeric complex or coordination polymer of claim 1, wherein the at least one N,N,N',N'-tetra(4-pyridyl)-1,4-phenylenediamine ligand is designated as $L^1$, and the oligomeric complex or coordination polymer includes at least one of $Zn_2L^1Cl_4$, $Zn_2L^1Br_4 \cdot MeOH$, $Zn_2L^1I_4$, $[CdL^1Cl_2]_n \cdot nH_2O$, $[CdL^1Br_2] \cdot 7.5H_2O$, $[CdL^1I_2]_n$, $HgL^1Cl_2]_n$, $[HgL^1Br_2]_n$, or $HgL^1I_2$, wherein n is an integer of 2 or more.

4. The oligomeric complex or coordination polymer of claim 1, wherein at least one metal atom comprises at least one of zinc, cadmium, silver or mercury.

5. The oligomeric complex or coordination polymer of claim 1, wherein at least one metal atom comprises at least one metal atom structurally incorporated between two ligands.

6. The oligomeric complex or coordination polymer of claim 1, wherein at least two of the ligands are N,N,N',N'-tetra(4-pyridyl)-1,4-phenylenediamine ligands.

7. The oligomeric complex or coordination polymer of claim 6, comprising at least one metal atom structurally incorporated between two N,N,N',N'-tetra(4-pyridyl)-1,4-phenylenediamine ligands.

8. The oligomeric complex or coordination polymer of claim 1, wherein each ligand of the oligomeric complex or coordination polymer is N,N,N',N'-tetra(4-pyridyl)-1,4-phenylenediamine.

9. The oligomeric complex or coordination polymer of claim 8, wherein each N,N,N',N'-tetra(4-pyridyl)-1,4-phenylenediamine ligand is designated as $L^1$, and the oligomeric complex or coordination polymer includes at least one of $Zn_2L^1Cl_4$, $Zn_2L^1Br_4 \cdot MeOH$, $Zn_2L^1I_4$, $[CdL^1Cl_2]_n \cdot nH_2O$, $[CdL^1Br_2] \cdot 7.5H_2O$, $[CdL^1I_2]_n$, $[HgL^1Cl_2]_n$, $[HgL^1Br_2]_n$, or $HgL^1I_2$, wherein n is an integer of 2 or more.

10. The oligomeric complex or coordination polymer of claim 1, wherein the coordination polymer emits visible light upon exposure to UV light.

11. The oligomeric complex or coordination polymer of claim 1, wherein the at least two ligands comprise at least one N,N,N',N'-tetra(4-pyridyl)-1,4-phenylenediamine and at least one N,N-di(2-pyridyi)-N',N'-di(4-pyridyl)-1,4-phenylenediamine.

12. A method of preparing an oligomeric complex or a coordination polymer, the method comprising:
   providing at least two ligands, wherein at least one of the at least two ligands comprises N,N,N',N'-tetra(4-pyridyl)-1,4-phenylenediamine;
   providing at least two metal atoms; and
   contacting the at least two ligands and the at least two metal atoms under conditions suitable to form an oligomeric complex or coordination polymer of the at least two ligands and the at least two metal atoms.

13. The method of claim 12, wherein providing the at least two metal atoms comprises providing at least one zinc salt, at least one cadmium salt, at least one mercury salt, at least one silver salt, or mixtures thereof.

14. An oligomeric complex or a coordination polymer comprising:
   at least two ligands, wherein each of the at least two ligands comprises N,N,N',N'-tetra(4-pyridyl)-1,4-phenylenediamine; and
   at least one metal atom structurally incorporated with the ligands.

* * * * *

UNITED STATES PATENT AND TRADEMARK OFFICE
CERTIFICATE OF CORRECTION

| | |
|---|---|
| PATENT NO. | : 8,653,230 B2 |
| APPLICATION NO. | : 13/030344 |
| DATED | : February 18, 2014 |
| INVENTOR(S) | : Xie |

It is certified that error appears in the above-identified patent and that said Letters Patent is hereby corrected as shown below:

On the title page, item (56), under "OTHER PUBLICATIONS", in Column 2, Line 1, delete "et al" and insert -- et al. --, therefor.

In the Drawings

Delete Drawing Sheet 11 of 13 and substitute therefor with the attached Drawing Sheet 11 of 13 consisting of replacement FIG. 14.

In the Specifications

In Column 5, Line 28, delete "bipyrdyl" and insert -- bipyridyl --, therefor.

In Column 5, Line 49, delete "($Py^3Py^4NH$)" and insert -- ($Py^1Py^2NH$) --, therefor.

In Column 12, Line 49, delete "Cd(NO3)2.4H2O" and insert -- $Cd(NO_3)_2.4H_2O$ --, therefor.

In Column 15, Line 56, delete "$[CdL^1Cl_2]_nnH_2O$" and insert -- $[CdL^1Cl_2]_n.nH_2O$ --, therefor.

In Column 16, Line 43, delete "coordination polymer 1100" and insert -- coordination polymer 1110 --, therefor.

In Column 17, Line 3, delete "Elmentar" and insert -- Elementar --, therefor.

In Column 18, Line 7, delete "466(m)" and insert -- 466(m). --, therefor.

In Column 18, Line 51, delete "(br, H2O)," and insert -- (br, $H_2O$), --, therefor.

Signed and Sealed this
Twenty-sixth Day of August, 2014

Michelle K. Lee
*Deputy Director of the United States Patent and Trademark Office*

In Column 19, Line 26, delete "H2O" and insert -- $H_2O$ --, therefor.

In Column 20, Lines 43-44, delete "$[Cd_4(L2)_4Cl_8]_n \cdot 2nDMF$ (13)" and insert -- $[Cd_4(L_2)_4Cl_8]_n \cdot 2nDMF$ (13) --, therefor.

In Column 22, Line 10, delete "L1, L2," and insert -- $L^1$, $L^2$, --, therefor.

In Column 22, Line 17, delete "L1" and insert -- $L^1$ --, therefor.

In Column 22, Line 29, delete "L1" and insert -- $L^1$ --, therefor.

In Column 24, Line 2, delete "R/w" and insert -- R/W --, therefor.

In the Claims

In Column 29, Line 7, in Claim 11, delete "N,N-di(2-pyridyi)-N'," and insert -- N,N-di(2-pyridyl)-N', --, therefor.